United States Patent
Wolinsky et al.

(10) Patent No.: US 10,390,714 B2
(45) Date of Patent: *Aug. 27, 2019

(54) DEVICES FOR FIXING A SENSOR IN A LUMEN

(75) Inventors: Lone Wolinsky, Ramat Gan (IL); Alon Ben-Yoseph, Amek Ylsrael (IL); Abraham Penner, Tel Aviv (IL)

(73) Assignee: Remon Medical Technologies, LTD., Caesarea (IL)

( * ) Notice: Subject to any disclaimer, the term of this patent is extended or adjusted under 35 U.S.C. 154(b) by 1327 days.

This patent is subject to a terminal disclaimer.

(21) Appl. No.: 11/559,868

(22) Filed: Nov. 14, 2006

(65) Prior Publication Data

US 2007/0129637 A1 Jun. 7, 2007

Related U.S. Application Data

(63) Continuation-in-part of application No. 11/034,502, filed on Jan. 12, 2005, now Pat. No. 7,572,228.

(Continued)

(51) Int. Cl.
*A61B 5/00* (2006.01)
*A61F 2/82* (2013.01)
*A61B 5/0215* (2006.01)

(52) U.S. Cl.
CPC ........ *A61B 5/02152* (2013.01); *A61B 5/6882* (2013.01); *A61B 5/0215* (2013.01);
(Continued)

(58) Field of Classification Search
CPC ....... A61B 5/68; A61B 5/6846; A61B 5/6847; A61B 5/686; A61B 5/6862; A61B 5/6876; A61B 5/6882; A61B 5/0215
See application file for complete search history.

(56) References Cited

U.S. PATENT DOCUMENTS

| 2,463,533 | A | 3/1949 | Harrison, et al. |
| 3,805,796 | A | 4/1974 | Davies et al. |
| | | (Continued) | |

FOREIGN PATENT DOCUMENTS

| EP | 0897690 | 2/1999 |
| EP | 0928598 A2 | 7/1999 |
| | (Continued) | |

OTHER PUBLICATIONS

Implantation of balloon-expandable intravascular grafts by catheterization in pulmonary arteries and systemic veins C E Mullins; M P O'Laughlin; G W Vick 3rd; D C Mayer; T J Myers; D L Kearney; R A Schatz; J C Palmaz Circulation, 1988; 77: 188-199.*

(Continued)

*Primary Examiner* — Christian Jang
*Assistant Examiner* — Karen E Toth
(74) *Attorney, Agent, or Firm* — Faegre Baker Daniels LLP

(57) ABSTRACT

Sensing devices and methods of implanting sensing devices within an anatomical vessel network of a patient are provided. In one method, a fixation element (e.g., a stent or coil) of the sensing device is expanded into firm contact with a wall of a main anatomical vessel (e.g., a right pulmonary artery), and a stabilization element of the sensing device is placed into contact with a wall of an anatomical vessel branch of the main anatomical vessel. In another method, a first fixation element of the sensing device is expanded into firm contact with the wall of the main anatomical vessel (e.g., a right pulmonary artery) at a longitudinal location proximal to the anatomical vessel branch, and a second fixation element of the sensing device is expanded into firm contact with the wall of the main anatomical vessel at a longitudinal location distal to the anatomical vessel branch.

15 Claims, 14 Drawing Sheets

Related U.S. Application Data

(60) Provisional application No. 60/737,131, filed on Nov. 15, 2005.

(52) U.S. Cl.
CPC .......... *A61B 5/6862* (2013.01); *A61B 5/6876* (2013.01); *A61F 2/82* (2013.01)

(56) References Cited

U.S. PATENT DOCUMENTS

| | | | |
|---|---|---|---|
| 3,874,388 A | 4/1975 | King et al. | |
| 4,256,115 A | 3/1981 | Bilitch | |
| 4,391,124 A | 7/1983 | Drost et al. | |
| 4,407,296 A | 10/1983 | Anderson | |
| 4,485,813 A | 12/1984 | Anderson et al. | |
| 4,492,107 A | 1/1985 | Sandhu | |
| 4,672,976 A | 6/1987 | Kroll | |
| 4,836,204 A | 6/1989 | Landymore et al. | |
| 4,846,191 A | 7/1989 | Brockway et al. | |
| 4,886,065 A | 12/1989 | Collins, Jr. | |
| 4,900,303 A | 2/1990 | Lemelson | |
| 4,917,089 A | 4/1990 | Sideris | |
| 4,966,148 A | 10/1990 | Millar | |
| 5,040,538 A | 8/1991 | Mortazavi | |
| 5,218,965 A | 6/1993 | Ring | |
| 5,284,138 A | 2/1994 | Kujawski | |
| 5,303,207 A | 4/1994 | Brady et al. | |
| 5,334,217 A | 8/1994 | Das | |
| 5,411,551 A | 5/1995 | Winston et al. | |
| 5,415,630 A | 5/1995 | Gory et al. | |
| 5,433,736 A | 7/1995 | Nilsson | |
| 5,438,554 A | 8/1995 | Seyed-Bolorforosh et al. | |
| 5,451,235 A | 9/1995 | Lock et al. | |
| 5,509,900 A | 4/1996 | Kirkman et al. | |
| 5,601,600 A | 2/1997 | Ton | |
| 5,604,531 A | 2/1997 | Iddan et al. | |
| 5,634,936 A | 6/1997 | Linden et al. | |
| 5,656,036 A | 8/1997 | Palmaz | |
| 5,662,711 A | 9/1997 | Douglas | |
| 5,704,352 A | 1/1998 | Tremblay et al. | |
| 5,725,552 A | 3/1998 | Kotula et al. | |
| 5,733,249 A | 3/1998 | Katzin et al. | |
| 5,733,294 A | 3/1998 | Forber et al. | |
| 5,733,313 A | 3/1998 | Barreras, Sr. et al. | |
| 5,749,909 A | 5/1998 | Schroeppel et al. | |
| 5,772,669 A | 6/1998 | Vrba | |
| 5,775,331 A | 7/1998 | Raymond et al. | |
| 5,776,168 A | 7/1998 | Gunderson | |
| 5,800,497 A | 9/1998 | Bakels et al. | |
| 5,824,053 A | 10/1998 | Khosravi et al. | |
| 5,833,603 A | 11/1998 | Kovacs et al. | |
| 5,855,563 A | 1/1999 | Kaplan et al. | |
| 5,860,923 A | 1/1999 | Lenker et al. | |
| 5,891,154 A | 4/1999 | Loeffler | |
| 5,967,980 A | 10/1999 | Ferre et al. | |
| 5,967,986 A | 10/1999 | Cimochowski et al. | |
| 5,967,989 A | 10/1999 | Cimochowski et al. | |
| 5,995,876 A | 11/1999 | Kruse et al. | |
| 6,002,969 A * | 12/1999 | Machek et al. | 607/122 |
| 6,015,386 A | 1/2000 | Kensey et al. | |
| 6,015,387 A | 1/2000 | Schwartz et al. | |
| 6,030,413 A | 2/2000 | Lazarus | |
| 6,033,366 A | 3/2000 | Brockway et al. | |
| 6,053,873 A | 4/2000 | Govari et al. | |
| 6,056,775 A * | 5/2000 | Borghi | A61F 2/856 606/195 |
| 6,076,016 A | 6/2000 | Feierbach | |
| 6,077,227 A | 6/2000 | Miesel et al. | |
| 6,097,984 A | 8/2000 | Douglas | |
| 6,106,464 A | 8/2000 | Bass et al. | |
| 6,140,740 A | 10/2000 | Porat et al. | |
| 6,159,156 A | 12/2000 | Van Bockel | |
| 6,179,858 B1 | 1/2001 | Squire et al. | |
| 6,193,745 B1 | 2/2001 | Fogarty et al. | |
| 6,214,025 B1 | 4/2001 | Thistle et al. | |
| 6,231,516 B1 | 5/2001 | Keilman | |
| 6,236,889 B1 | 5/2001 | Soykan et al. | |
| 6,239,724 B1 | 5/2001 | Doron et al. | |
| 6,240,312 B1 | 5/2001 | Alfano et al. | |
| 6,246,898 B1 | 6/2001 | Vesely et al. | |
| 6,277,078 B1 | 8/2001 | Porat et al. | |
| 6,278,790 B1 | 8/2001 | Davis et al. | |
| 6,309,350 B1 | 10/2001 | Van Tassel | |
| 6,328,669 B1 | 12/2001 | Imanishi et al. | |
| 6,328,699 B1 * | 12/2001 | Eigler et al. | 600/486 |
| 6,331,183 B1 | 12/2001 | Kaplan | |
| 6,379,308 B1 | 4/2002 | Brockway et al. | |
| 6,409,674 B1 | 6/2002 | Brockway et al. | |
| 6,416,474 B1 | 7/2002 | Penner et al. | |
| 6,432,050 B1 | 8/2002 | Porat et al. | |
| 6,442,413 B1 | 8/2002 | Silver | |
| 6,447,522 B2 | 9/2002 | Gambale et al. | |
| 6,472,991 B1 | 10/2002 | Schulman et al. | |
| 6,475,170 B1 | 11/2002 | Doran et al. | |
| 6,486,588 B2 | 11/2002 | Doron et al. | |
| 6,522,926 B1 | 2/2003 | Kieval et al. | |
| 6,527,780 B1 | 3/2003 | Wallace et al. | |
| 6,543,272 B1 | 4/2003 | Vitek | |
| 6,585,763 B1 | 7/2003 | Keilman et al. | |
| 6,592,553 B2 | 7/2003 | Zhang et al. | |
| 6,628,989 B1 | 9/2003 | Penner et al. | |
| 6,645,143 B2 | 11/2003 | Van Tassel et al. | |
| 6,660,021 B1 | 12/2003 | Palmer et al. | |
| 6,685,638 B1 | 2/2004 | Taylor et al. | |
| 6,699,186 B1 | 3/2004 | Wolinsky et al. | |
| 6,702,847 B2 | 3/2004 | DiCarlo | |
| 6,730,108 B2 | 5/2004 | Van Tassel et al. | |
| 6,738,671 B2 | 5/2004 | Christophersom et al. | |
| 6,743,173 B2 | 6/2004 | Penner et al. | |
| 6,746,404 B2 | 6/2004 | Schwartz | |
| 6,747,916 B1 | 6/2004 | Fluery et al. | |
| 6,755,855 B2 | 6/2004 | Yurek et al. | |
| 6,764,446 B2 | 7/2004 | Wolinsky et al. | |
| 6,783,499 B2 | 8/2004 | Schwartz | |
| 6,800,060 B2 | 10/2004 | Marshall | |
| 6,840,956 B1 | 1/2005 | Wolinsky et al. | |
| 6,855,115 B2 | 2/2005 | Fonseca et al. | |
| 6,868,288 B2 | 3/2005 | Thompson | |
| 6,890,303 B2 | 5/2005 | Fitz | |
| 6,899,729 B1 | 5/2005 | Cox | |
| 6,904,308 B2 | 6/2005 | Frisch et al. | |
| 6,920,347 B2 | 7/2005 | Simon et al. | |
| 6,934,573 B1 | 8/2005 | Glukhovsky et al. | |
| 6,950,690 B1 | 9/2005 | Meron et al. | |
| 6,958,034 B2 | 10/2005 | Iddan | |
| 6,970,742 B2 | 11/2005 | Mann et al. | |
| 6,972,017 B2 | 12/2005 | Smith et al. | |
| 6,984,205 B2 | 1/2006 | Gazdzinski | |
| 7,001,329 B2 | 2/2006 | Kobayashi et al. | |
| 7,006,858 B2 | 2/2006 | Silver et al. | |
| 7,009,634 B2 | 3/2006 | Iddan et al. | |
| 7,011,671 B2 | 3/2006 | Welch | |
| 7,024,248 B2 | 4/2006 | Penner et al. | |
| 7,033,322 B2 * | 4/2006 | Silver | 600/486 |
| 7,035,684 B2 | 4/2006 | Lee | |
| 7,039,453 B2 | 5/2006 | Mullick et al. | |
| 7,060,038 B2 | 6/2006 | Letort et al. | |
| 7,064,472 B2 | 6/2006 | Peline et al. | |
| 7,065,409 B2 | 6/2006 | Mazar | |
| 7,065,709 B2 | 6/2006 | Ellis et al. | |
| 7,076,305 B2 | 7/2006 | Imran et al. | |
| 7,083,822 B2 | 8/2006 | Brightbill | |
| 7,116,352 B2 | 10/2006 | Yaron | |
| 7,118,529 B2 | 10/2006 | Glukhovsky et al. | |
| 7,118,531 B2 | 10/2006 | Krill | |
| 7,131,986 B2 | 11/2006 | Sirhan et al. | |
| 7,160,258 B2 | 1/2007 | Imran et al. | |
| 7,181,261 B2 | 2/2007 | Silver et al. | |
| 7,198,603 B2 | 4/2007 | Penner et al. | |
| 7,211,045 B2 | 5/2007 | Dala-Krish et al. | |
| 7,273,457 B2 | 9/2007 | Penner | |
| 7,283,874 B2 | 10/2007 | Penner | |
| 7,308,319 B2 | 12/2007 | Lovett et al. | |

(56) References Cited

U.S. PATENT DOCUMENTS

| | | | |
|---|---|---|---|
| 7,338,512 B2 | 3/2008 | McGuckin, Jr. et al. | |
| 7,347,868 B2 | 3/2008 | Burnett et al. | |
| 7,392,094 B2 | 6/2008 | Zhang et al. | |
| 7,437,193 B2 | 10/2008 | Parramon et al. | |
| 7,452,334 B2 | 11/2008 | Gianchandani et al. | |
| 7,477,946 B2 | 1/2009 | Tockman | |
| 7,555,351 B2 | 6/2009 | Zhang et al. | |
| 7,572,228 B2* | 8/2009 | Wolinsky et al. | 600/486 |
| 7,744,542 B2 | 6/2010 | Piaget et al. | |
| 7,780,694 B2 | 8/2010 | Palmer et al. | |
| 7,850,708 B2 | 12/2010 | Pal | |
| 7,890,188 B2 | 2/2011 | Zhang et al. | |
| 7,930,031 B2 | 4/2011 | Penner | |
| 8,271,093 B2 | 9/2012 | Von Arx et al. | |
| 8,577,460 B2 | 11/2013 | Penner | |
| 8,934,972 B2 | 1/2015 | Penner | |
| 9,026,229 B2 | 5/2015 | Stalker et al. | |
| 9,149,193 B2 | 10/2015 | Wolinsky et al. | |
| 2001/0004699 A1* | 6/2001 | Gittings | A61B 17/11 606/153 |
| 2002/0038135 A1 | 3/2002 | Connelly et al. | |
| 2002/0042650 A1* | 4/2002 | Vardi | A61F 2/82 623/1.35 |
| 2002/0045920 A1 | 4/2002 | Thompson | |
| 2002/0045921 A1 | 4/2002 | Wolinsky et al. | |
| 2002/0077555 A1* | 6/2002 | Schwartz | 600/486 |
| 2002/0077673 A1 | 6/2002 | Penner et al. | |
| 2002/0123672 A1 | 9/2002 | Christophersom et al. | |
| 2002/0151816 A1 | 10/2002 | Rich et al. | |
| 2002/0165601 A1 | 11/2002 | Clerc | |
| 2002/0169584 A1 | 11/2002 | Fu et al. | |
| 2002/0183628 A1 | 12/2002 | Reich et al. | |
| 2002/0188207 A1 | 12/2002 | Richter | |
| 2003/0036755 A1 | 2/2003 | Ginn | |
| 2003/0114897 A1 | 6/2003 | Von Arx et al. | |
| 2003/0139796 A1 | 7/2003 | Sequin et al. | |
| 2003/0195606 A1* | 10/2003 | Davidson et al. | 623/1.11 |
| 2003/0233095 A1 | 12/2003 | Urbanski et al. | |
| 2004/0006377 A1 | 1/2004 | Behm | |
| 2004/0054403 A1* | 3/2004 | Israel | 623/1.35 |
| 2004/0116992 A1 | 6/2004 | Wardle et al. | |
| 2004/0147969 A1 | 7/2004 | Mann et al. | |
| 2004/0176672 A1 | 9/2004 | Silver et al. | |
| 2004/0204744 A1 | 10/2004 | Penner et al. | |
| 2004/0215228 A1 | 10/2004 | Simpson et al. | |
| 2005/0080346 A1 | 4/2005 | Gianchandani et al. | |
| 2005/0080472 A1 | 4/2005 | Atkinson et al. | |
| 2005/0096702 A1 | 5/2005 | Denker et al. | |
| 2005/0109338 A1 | 5/2005 | Stahmann et al. | |
| 2005/0115561 A1 | 6/2005 | Stahmann et al. | |
| 2005/0124875 A1 | 6/2005 | Kawano et al. | |
| 2005/0136385 A1 | 6/2005 | Mann et al. | |
| 2005/0149108 A1 | 7/2005 | Cox | |
| 2005/0149128 A1 | 7/2005 | Heil, Jr. et al. | |
| 2005/0149155 A1 | 7/2005 | Scheiner et al. | |
| 2005/0149156 A1 | 7/2005 | Libbus et al. | |
| 2005/0154321 A1 | 7/2005 | Wolinsky et al. | |
| 2005/0165456 A1 | 7/2005 | Mann et al. | |
| 2005/0182387 A1 | 8/2005 | Webler | |
| 2005/0203444 A1 | 9/2005 | Schonenberger et al. | |
| 2005/0209678 A1 | 9/2005 | Henkes et al. | |
| 2005/0245840 A1 | 11/2005 | Christopherson et al. | |
| 2005/0249776 A1* | 11/2005 | Chen | A61L 31/10 424/423 |
| 2005/0265999 A1 | 12/2005 | Bush et al. | |
| 2006/0009818 A1 | 1/2006 | Von Arx et al. | |
| 2006/0047205 A1 | 3/2006 | Ludomirsky et al. | |
| 2006/0064133 A1 | 3/2006 | Von Arx et al. | |
| 2006/0064134 A1 | 3/2006 | Mazar et al. | |
| 2006/0064142 A1 | 3/2006 | Chavan et al. | |
| 2006/0064143 A1 | 3/2006 | Von Arx et al. | |
| 2006/0079740 A1* | 4/2006 | Silver | A61B 5/0031 600/309 |
| 2006/0089627 A1 | 4/2006 | Burnett et al. | |
| 2006/0089694 A1 | 4/2006 | Zhang et al. | |
| 2006/0122522 A1* | 6/2006 | Chavan et al. | 600/505 |
| 2006/0136004 A1 | 6/2006 | Cowan et al. | |
| 2006/0142819 A1 | 6/2006 | Penner et al. | |
| 2006/0149329 A1 | 7/2006 | Penner | |
| 2006/0149330 A1 | 7/2006 | Mann et al. | |
| 2006/0178586 A1 | 8/2006 | Dobak, III | |
| 2006/0200031 A1* | 9/2006 | White et al. | 600/486 |
| 2006/0206153 A1 | 9/2006 | Libbus et al. | |
| 2006/0241735 A1 | 10/2006 | Tockman et al. | |
| 2006/0259085 A1* | 11/2006 | Zhang et al. | 607/9 |
| 2006/0287700 A1 | 12/2006 | White et al. | |
| 2006/0293741 A1 | 12/2006 | Johnson et al. | |
| 2007/0049833 A1 | 3/2007 | Tearney et al. | |
| 2007/0055313 A1 | 3/2007 | Stahmann et al. | |
| 2007/0060959 A1* | 3/2007 | Salo et al. | 607/6 |
| 2007/0156126 A1 | 7/2007 | Flaherty | |
| 2007/0156205 A1 | 7/2007 | Larson et al. | |
| 2007/0162090 A1 | 7/2007 | Penner | |
| 2007/0179583 A1 | 8/2007 | Goetzinger et al. | |
| 2007/0191904 A1 | 8/2007 | Libbus et al. | |
| 2007/0208390 A1 | 9/2007 | Von Arx et al. | |
| 2007/0250126 A1 | 10/2007 | Maile et al. | |
| 2007/0274565 A1 | 11/2007 | Penner | |
| 2007/0282413 A1 | 12/2007 | Tockman et al. | |
| 2007/0282415 A1 | 12/2007 | Tockman et al. | |
| 2008/0071178 A1 | 3/2008 | Greenland et al. | |
| 2008/0071248 A1 | 3/2008 | Delgado et al. | |
| 2008/0071339 A1 | 3/2008 | Stalker et al. | |
| 2008/0108904 A1 | 5/2008 | Heil | |
| 2008/0176271 A1 | 7/2008 | Silver et al. | |
| 2008/0243007 A1 | 10/2008 | Liao et al. | |
| 2008/0275350 A1 | 11/2008 | Liao et al. | |
| 2008/0283066 A1 | 11/2008 | Delgado et al. | |
| 2009/0054793 A1 | 2/2009 | Nunez et al. | |
| 2009/0171274 A1 | 7/2009 | Harlev et al. | |
| 2009/0270742 A1 | 10/2009 | Wolinsky et al. | |
| 2010/0016840 A1 | 1/2010 | Stahmann et al. | |
| 2010/0210923 A1 | 8/2010 | Li et al. | |
| 2015/0201848 A1 | 7/2015 | Stalker et al. | |

FOREIGN PATENT DOCUMENTS

| | | |
|---|---|---|
| EP | 1068836 | 1/2001 |
| EP | 1488735 | 6/2007 |
| GB | 2333044 | 7/1999 |
| JP | H(11)-089942 | 4/1999 |
| JP | 2000-507142 | 6/2000 |
| JP | 2001-061790 | 3/2001 |
| JP | 2002515807 A | 5/2002 |
| JP | 2004041724 A | 2/2004 |
| JP | 2006-500991 | 1/2006 |
| WO | WO1983/003348 | 10/1983 |
| WO | WO 99/34731 | 7/1999 |
| WO | WO9934453 A1 | 7/1999 |
| WO | WO2000/016686 | 3/2000 |
| WO | WO2000/059376 | 10/2000 |
| WO | WO2001/067989 | 9/2001 |
| WO | 2001076687 A2 | 10/2001 |
| WO | WO0174278 A2 | 10/2001 |
| WO | WO 01/87137 | 11/2001 |
| WO | WO 2004/024034 | 3/2004 |
| WO | WO 2004/110263 | 12/2004 |
| WO | WO 2005/058202 | 6/2005 |
| WO | WO2005/067817 | 7/2005 |
| WO | WO2006/062725 | 6/2006 |
| WO | WO 2007/062299 | 5/2007 |
| WO | WO2007/082115 | 7/2007 |
| WO | 2008002654 | 1/2008 |
| WO | WO2008/034077 | 3/2008 |
| WO | WO2008/057720 | 5/2008 |
| WO | WO2008/060197 | 5/2008 |
| WO | WO2008/144191 | 11/2008 |
| WO | 2009006610 | 1/2009 |

OTHER PUBLICATIONS https://www.collinsdictionary.com/dictionary/english/flange, retrieved Jan. 25, 2018.*

(56) References Cited

OTHER PUBLICATIONS https://www.collinsdictionary.com/dictionary/english/loop, retrieved Jan. 25, 2018.*

PCT International Search Report for PCT/IB2006/003183, Applicant: Remon Medical Technologies Ltd., Form PCT/ISA/210 and 220, dated Mar. 2, 2007 (6 pages).

PCT Written Opinion of the International Search Authority for PCT/IB2006/003183, Applicant: Remon Medical Technologies Ltd., Form PCT/ISA/237, dated Mar. 2, 2007 (5 pages).

Holmes et al. "SirolimusEluting Stents vs. Vascular Brachytherapy for InStent Restenosis Within BareMetal Stents" JAMA 295 (11): 1264-1273 Mar. 15, 2006.

Lanning & Shandas, "Development and Validation of Implantable Sensors for Monitoring Function of Prosthetic Heart Valves: In Vitro Studies", Medical & Biological Engineering & Computing, Jul. 2003, vol. 41, issue 4, pp. 416-424.

Sheth et al. "Subacute Thrombosis and Vascular Injury Resulting From Slotted-Tube Nitinol and Stainless Steel Stents in a Rabbit Carotid Artery Model" Circulation 1996, 94: 1733-1740.

Stone et al. "Paclitaxel-Eluting Stents vs.Vascular Brachytherapy for In-Stent Restenosis Within Bare-Metal Stents" JAMA 295(11): 1253-1263, Mar. 15, 2006.

Wenaweser et al. "Stent thrombosis following baremetal stent implantation: success of emergency percutaneous coronary intervention and predictors of adverse outcome" European Heart Journal 26: 1180-1187 2005.

PCT International Search Report for PCT/US2005/000041, Applicant: Remon Medical Technologies Ltd., forms PCT/ISA/210 and 220, dated Apr. 21, 2005.

PCT Written Opinion of the International Search Authority for PCT/US2005/000041 Applicant Remon Medical Technolgies Ltd., Form PCT/ISA/237, dated Apr. 21, 2005.

Goodall, Eleanor V. et al., "Position-Seletive Activation of Peripheral Nerve Fibers with a Cuff Electrode", IEEE Transactions on Biomedical Engineering, IEEE Service Center, Piscataway, NJ, US, vol. 43, No. 8, Aug. 1, 1996.

International Search Report and Written Opinion issued in PCT/US2010/020756, dated Sep. 27, 2010.

Invitation to Pay Fees and Partial Search Report issued in PCT/US2010/020756, dated May 12, 2010.

* cited by examiner

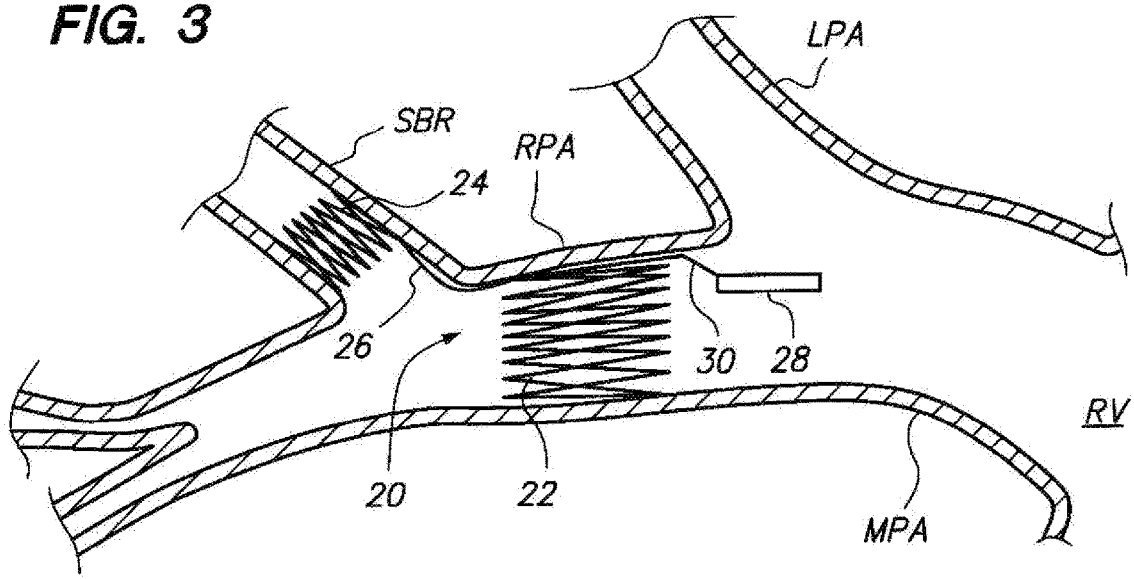
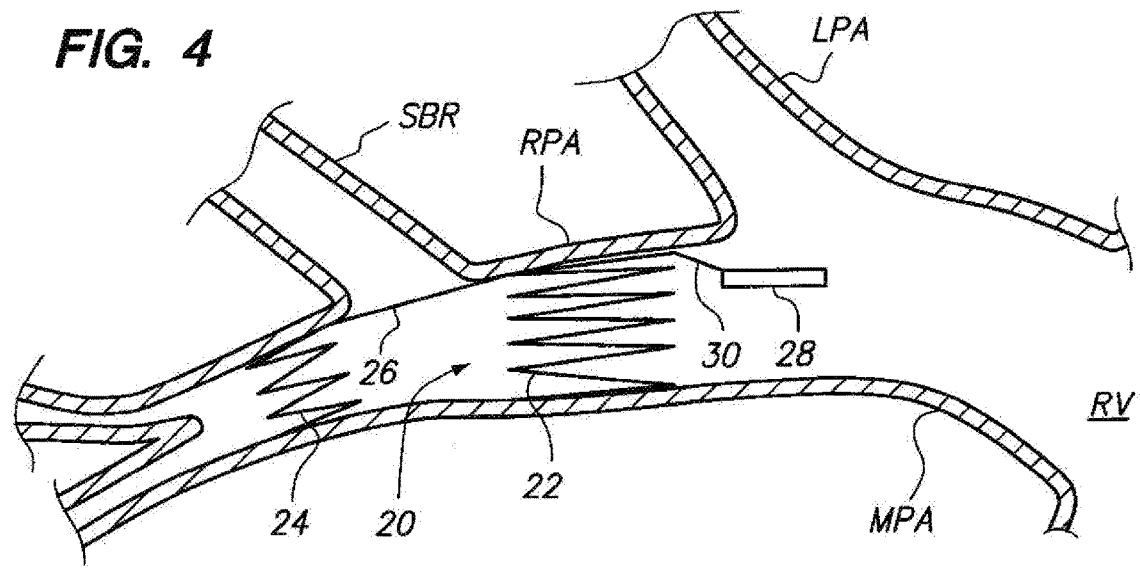

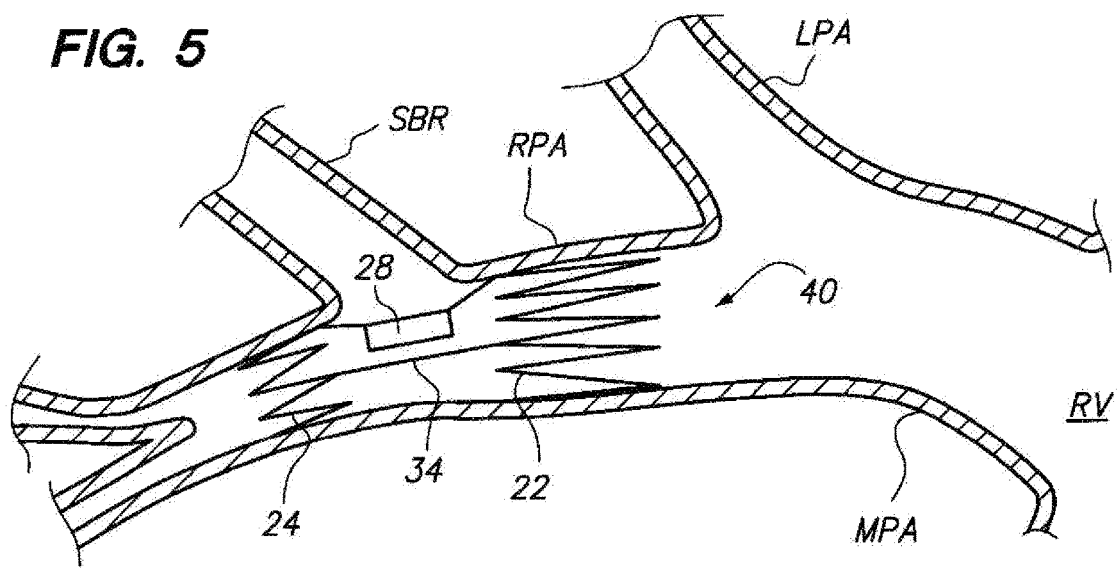
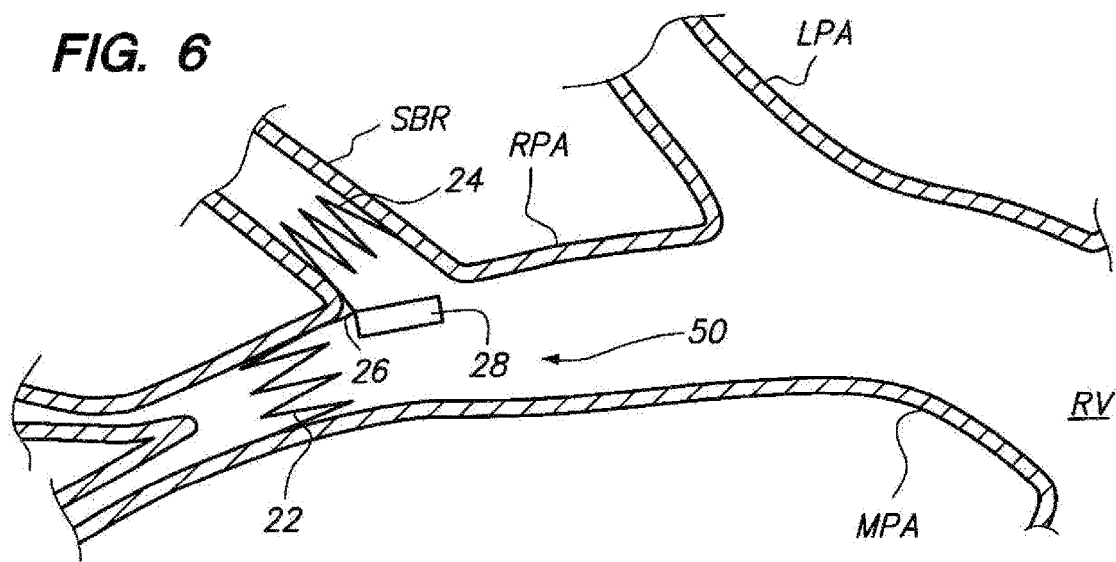

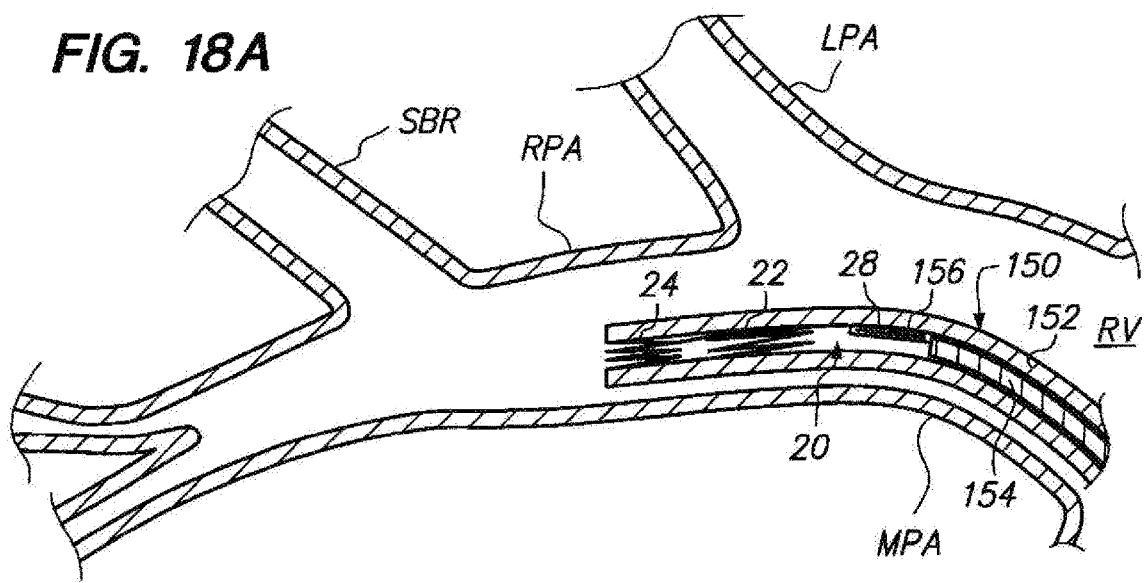
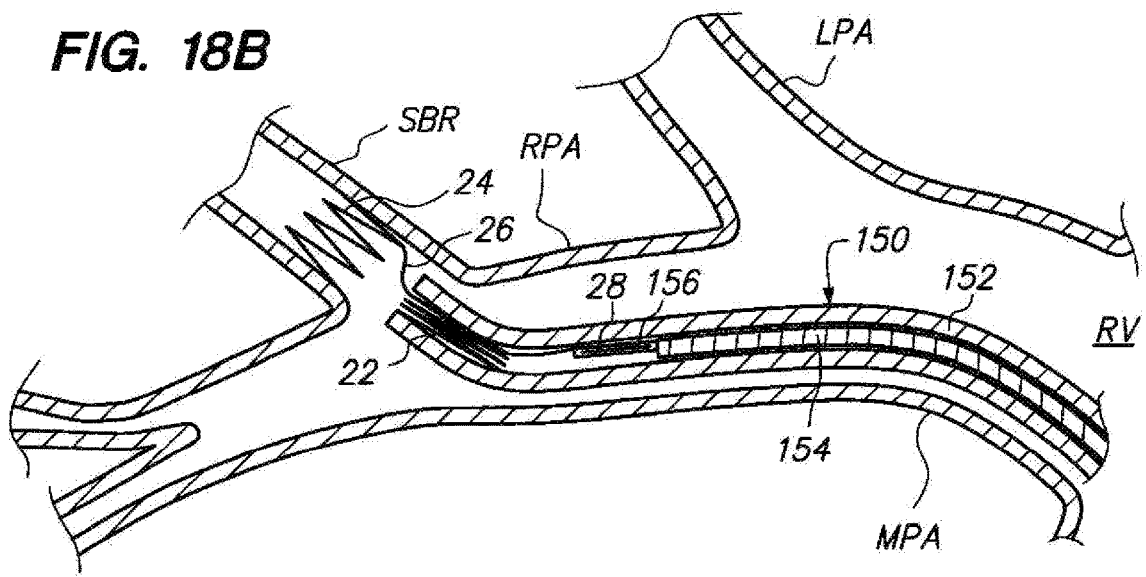

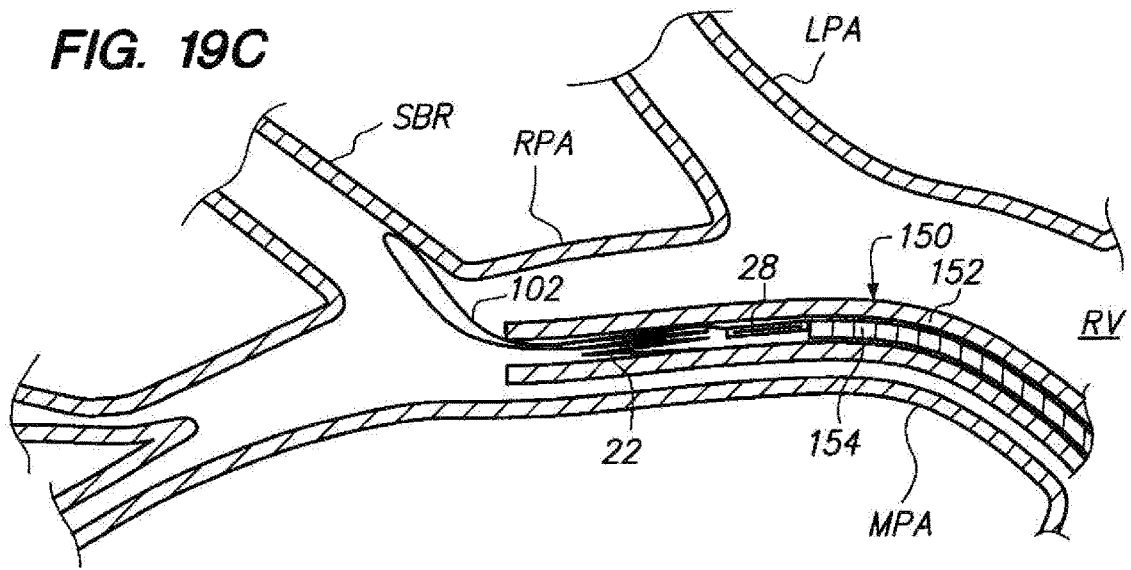
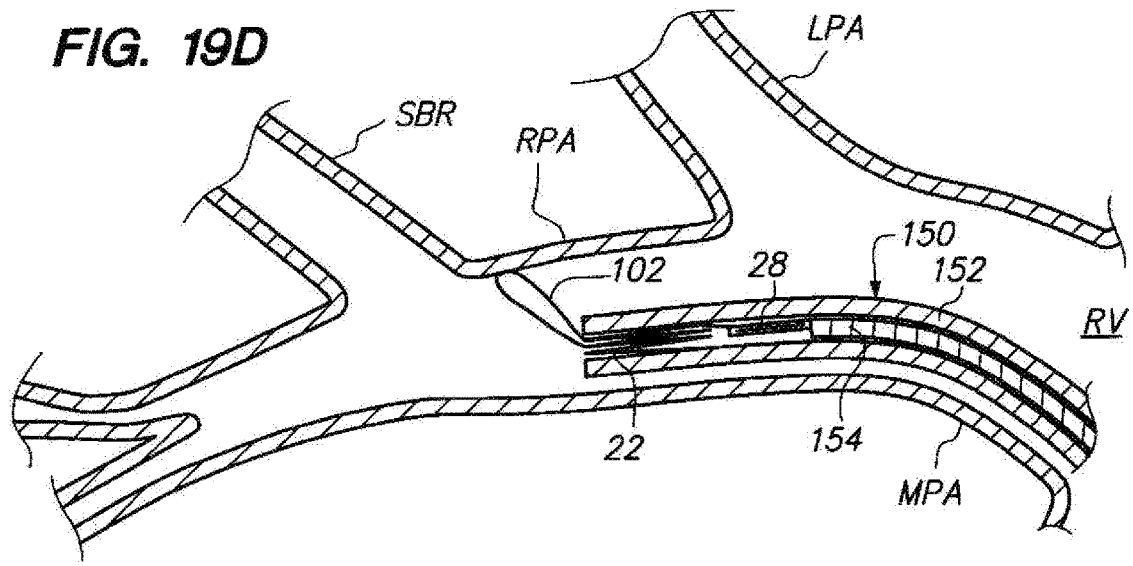

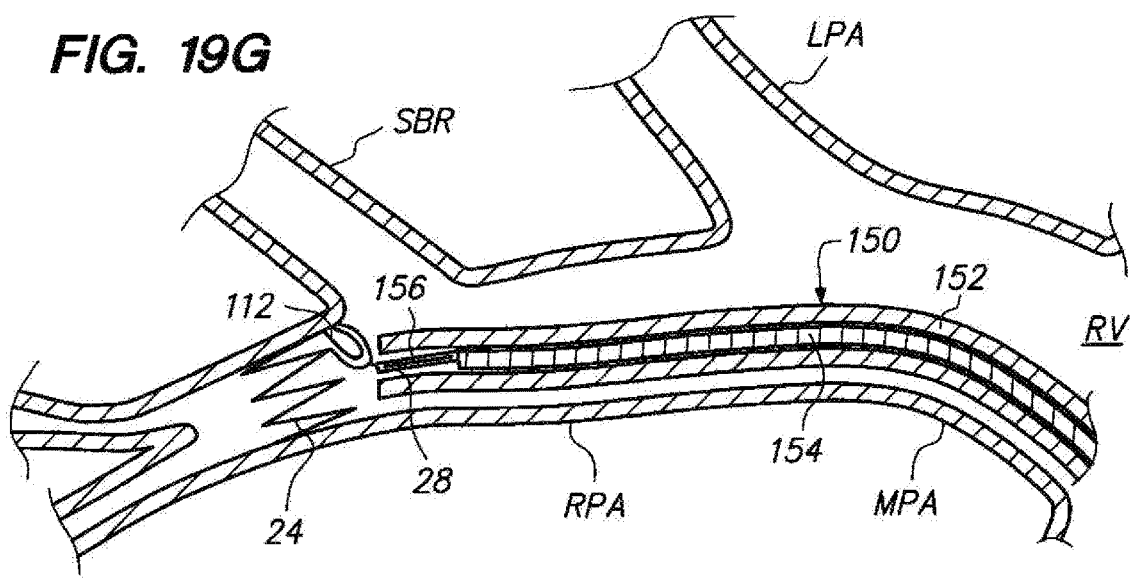
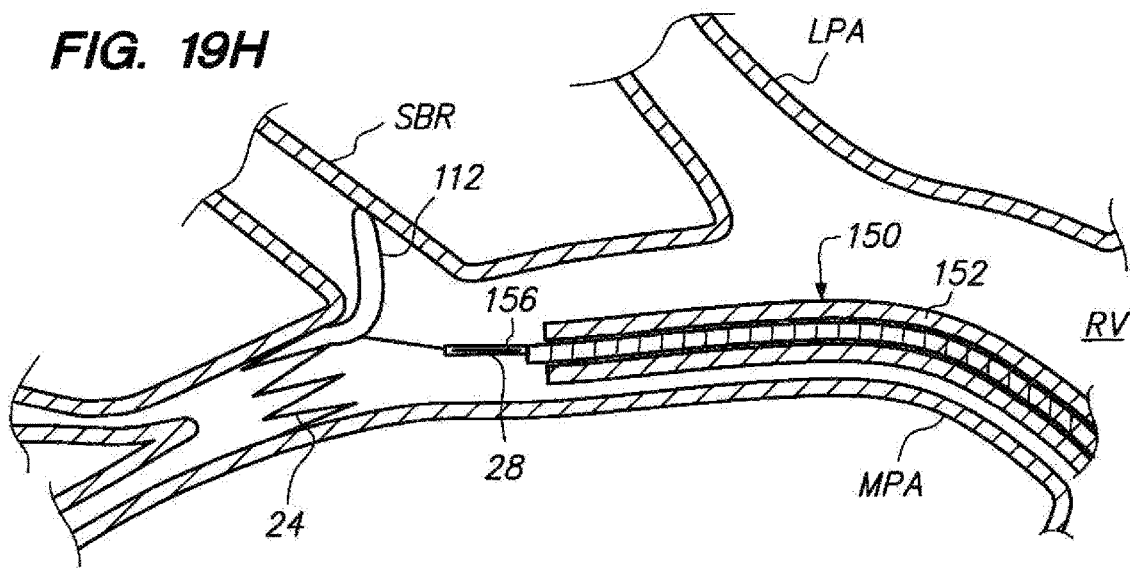

DEVICES FOR FIXING A SENSOR IN A LUMEN

RELATED APPLICATIONS

The application claims priority from U.S. Provisional Patent Application Ser. No. 60/737,131, filed Nov. 15, 2005, and is a continuation-in-part of U.S. patent application Ser. No. 11/034,502, filed Jan. 12, 2005, both of which are expressly incorporated herein by reference.

FIELD OF THE INVENTION

The invention relates to the field of implantable medical devices, and in particular, to devices and methods for positioning a sensor within the lumen of a blood vessel.

BACKGROUND OF THE INVENTION

The use of sensing devices in anatomical lumens is well known. For example, U.S. Pat. No. 4,485,813 describes a cardiac pacemaker sensor that can be permanently implanted in a specific location within a patient's body. U.S. Pat. Nos. 6,645,143, 6,053,873, and 6,442,413 and U.S. Patent Publication No. 2002/0188207 describe medical monitoring sensors designed to be permanently implanted in blood vessels and capable of sensing and transmitting via a telemetry link to an external monitor. The implanted sensing devices are utilized for monitoring physiological parameters within the patient's body.

Because the force created by the blood flow and/or heart movement, which may act on an implanted sensing device like a sail, tends to drag the sensing device longitudinally along the vessel, or rotate it in the case where the sensing device is implanted adjacent a bifurcation of a vessel branch, it is critical that the anchoring force created between the sensing device and the wall of the blood vessel be as great as possible. However, high local or radial force on the relative weak pulmonary artery vessel wall may cause perforation or aneurysm. Many of the vascular implantation techniques assume that the segment of the blood vessel in which the sensing device is intended to be implanted is straight (i.e., it has no branches). In some cases, however, the vessel segment may be branched. If the vessel segment adjacent the branch is long enough to accommodate the entire length of the sensing device, the sensing device may be implanted within the blood vessel without regard to the branch. If, however, the length of the vessel segment is limited, the sensing device may not be adequately implanted within the vessel segment without crossing the branch. In this case, the implanted sensing device may block future access to the vessel branch, e.g., during catheterization, may be unstable due to the transverse blood flow through the branch, and worse yet, may cause blood clots that may potentially result in an embolism. As a result, the length of the sensing device sufficient for affixation to the wall of the blood vessel may have to be reduced in order to accommodate the branched vessel. In addition, the diameters of many blood vessels are not uniform, and may even be conical, thereby presenting further challenges to lengthening the sensing device.

The right pulmonary artery, which is frequently the target of sensor implantation, such as for the purpose of monitoring hemodynamic parameters indicative of the efficiency of the heart or measure the glucose level of the blood, is both branched and non-uniform. For example, referring to FIG. 1, an implantable sensing device 10, which generally includes a fixation element 12 (e.g., a stent) and a sensing element 14 coupled to the fixation element 12, is shown implanted within the right pulmonary artery RPA of a patient. As shown by the arrows, blood flows from the right ventricle RV of the heart, out through the main pulmonary artery MPA, which branches into the right pulmonary artery RPA and a left pulmonary artery LPA. The sensing element 14, once implanted, may thus be capable of monitoring, e.g., the hemodynamic parameters of the blood flowing from the right ventricle RV.

As can be seen in FIG. 1, the right pulmonary artery RPA branches into various side branches SBR, none of which is crossed by the sensing device 10 to prevent the aforementioned problems from occurring. However, because the length of the implantable segment of the right pulmonary artery RPA (i.e., the segment between the point at which the right pulmonary artery RPA begins and the point at which the first side branch SBR, known anatomically as "Truncus anterior", begins) is relatively short (on average, about 40 mm), the length of the fixation element 12 must be relative short in order to accommodate the side branch SBR.

Because the length of the fixation element 12 must be relatively short, the stability of the sensing device 10 may be compromised. In addition, as can be seen from FIG. 1, the diameter of the right pulmonary artery RPA substantially decreases in the distal direction (i.e., from right to left), which causes the proximal end of the fixation element 12 to engage the vessel wall less firmly than the distal end of the fixation element 12 engages the vessel wall, thereby further compromising the stability of the sensing device 10.

There, thus, is a need to provide an improved technique for implanting a sensing device in a non-uniform and branched anatomical vessel.

SUMMARY OF THE INVENTION

In accordance with a first aspect of the present inventions, an implant for sensing parameters within an anatomical vessel network (e.g., the blood vessel network) of a patient is provided. The implant comprises a first fixation element having an expanded geometry for firmly engaging a wall of the vessel network at a first longitudinal location, and a second fixation element having an expanded geometry for firmly engaging the wall of vessel network at a second longitudinal location. The fixation elements can take the form of any suitable element, such as, e.g., a stent or a coil. The first and second longitudinal locations may be, e.g., in a single anatomical vessel, or respectively in a main anatomical vessel and an anatomical vessel branch of the main anatomical vessel. In one method, the vessel network has substantially differing diameters at the first and second longitudinal locations.

The implant further comprises a connecting element mechanically coupling the first and second fixation elements together in an articulating manner. The implant can optionally comprise a third fixation element having an expanded geometry for firmly engaging the wall of vessel network at a third longitudinal location, and another connecting element mechanically coupling the second and third fixation elements together in an articulating manner. While the present inventions should not be so limited in their broadest aspects, articulation of the fixation elements allows them to expand and move relative to each other, so that, e.g., they can be implanted within misaligned vessel segments (e.g., a main anatomical vessel and a branch of the anatomical vessel) or vessel segments with non-uniform diameters.

The implant further comprises a sensing element mechanically coupled to the first fixation element opposite the connecting element. The sensing element can be, e.g., one or more of a pressure sensor, an accelerometer, a position sensor, a wall motion sensor, a flow sensor, a temperature sensor, an oxygen sensor, a calcium sensor, a potassium sensor, a glucose sensor, a coagulation sensor, an electrical activity sensor, and a pH sensor. In an optional embodiment, the implant further comprises a transmitter configured for wirelessly transmitting information sensed by the sensing element to a remote receiver.

In accordance with a second aspect of the present inventions, a method of implanting a sensing device within an anatomical vessel network (e.g., a blood vessel network) of a patient is provided. The method comprises expanding a fixation element (e.g., a stent or coil) of the device into firm contact with a wall of a main anatomical vessel (e.g., a right pulmonary artery), and locating a stabilization element of the device into contact with a wall of an anatomical vessel branch of the main anatomical vessel. By way of non-limiting example, the stabilization element may be a second fixation element that is expanded into firm contact with the wall of the anatomical vessel branch or an element that resists rotation of the fixation element about a longitudinal axis of the main anatomical vessel. An optional method comprises expanding a third fixation element of the device into firm contact with the wall of the main anatomical vessel, wherein the first fixation element is located proximal to the anatomical vessel branch, and the third fixation element is located distal to the anatomical vessel branch. Optionally, the distal and or proximal anchor may have hooks for adding active fixation of the device minimizing potential migration.

In accordance with a third aspect of the present inventions, a method of implanting a sensing device within an anatomical vessel network (e.g., a blood vessel network) having a main anatomical vessel and an anatomical vessel branch of the main anatomical vessel is provided. The method comprises expanding a first fixation element of the device into firm contact with the wall of the main anatomical vessel (e.g., a right pulmonary artery) at a longitudinal location proximal to the anatomical vessel branch, and expanding a second fixation element of the device into firm contact with the wall of the main anatomical vessel at a longitudinal location distal to the anatomical vessel branch. The fixation elements can take the form of any suitable element, such as a stent or a coil. An optional method comprises expanding a third fixation element of the device into firm contact with the wall of the anatomical vessel branch.

The methods described above may optionally comprise locating a sensing element of the sensing device within the main anatomical vessel when the first fixation element is firmly engaged with the wall of the main anatomical vessel and the stabilization element is in contact with the wall of the anatomical vessel branch. The sensing element may be operated to measure, e.g., one or more of a pressure, acceleration, wall motion, fluid flow, temperature, oxygen level, glucose level, coagulation, electrical activity, and pH level within the anatomical vessel. Such measured information can be wirelessly transmitted from the sensing device.

While the present inventions should not be so limited in their broadest aspects, in accordance with the afore-described methods, the only portion of the sensing device within the bifurcation between the main anatomical vessel and the anatomical branch is the connecting element, which may have a relatively low profile. As a result, very little force will be applied to the sensing device by fluid flowing between the anatomical branch and the main anatomical vessel, thereby increasing the stability of the sensing device within the main anatomical vessel, and in the case where the fluid is blood, decreasing the chance of embolism that may otherwise result from clots formed by the obstructed blood flow. In addition, because the connecting element may have a low profile, future access to the anatomical branch is not significantly hindered, thereby preserving the capability of catheterizing the anatomical branch if necessary or desired. The connecting element allows the fixation elements to follow the anatomical vessel shape and movement, while preventing device migration. Also, the connecting elements enable a long, yet flexible, sensing device, thereby allowing easy delivery even through tortuous vessels, while its length prevents it from rotating into a bifurcation.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 3 is a side view of a second sensing device arrangement within the pulmonary arterial network in accordance with the present inventions;

FIG. 4 is a side view of a third sensing device arrangement within the pulmonary arterial network in accordance with the present inventions;

FIG. 5 is a side view of a fourth sensing device arrangement within the pulmonary arterial network in accordance with the present inventions;

FIG. 6 is a side view of a fifth sensing device arrangement within the pulmonary arterial network in accordance with the present inventions;

FIGS. 18A-18D are side views illustrating one method of implanting a sensing device within the pulmonary arterial network in accordance with the present inventions; and FIGS. 19A-19H are side views illustrating other methods of implanting a sensing device within the pulmonary arterial network in accordance with the present inventions.

DETAILED DESCRIPTION OF EMBODIMENTS

Figure 1:
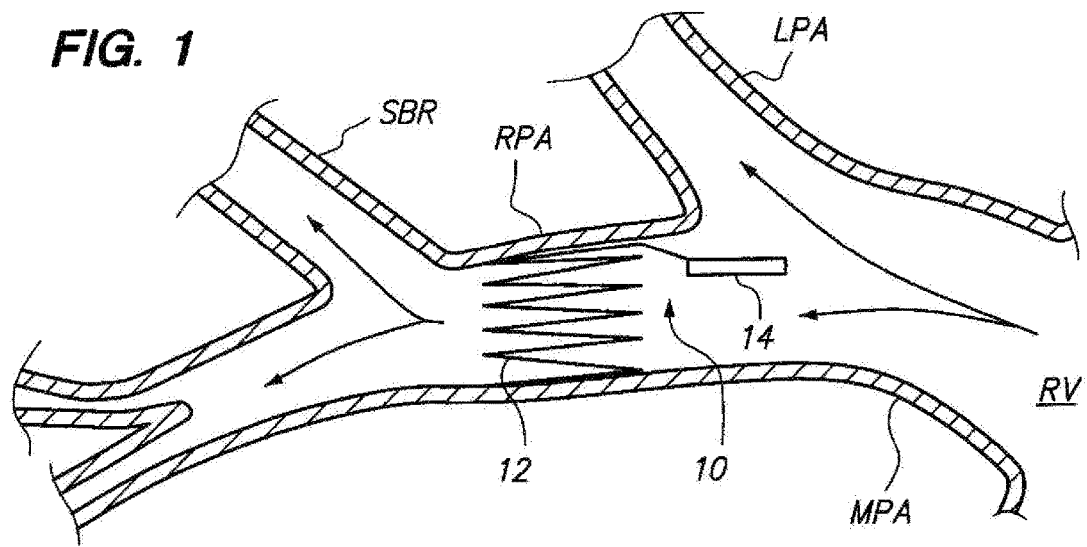
FIG. 1 is a side view of a prior art sensing device arrangement within a pulmonary arterial network of a patient.
Figure 2:
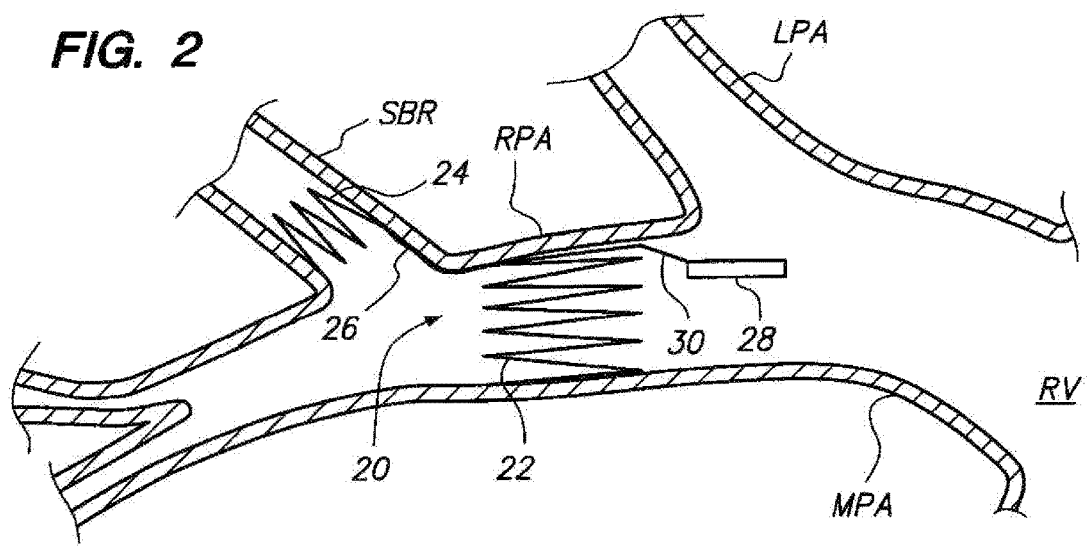
FIG. 2 is a side view of a first sensing device arrangement within the pulmonary arterial network in accordance with the present inventions.

Referring to FIG. 2, an implantable sensing device 20 constructed in accordance with the present inventions will now be described. The sensing device 20 is shown implanted within an anatomical vessel network, and in particular, the pulmonary arterial network of a patient. As previously described, blood flows from the right ventricle RV of the heart H, out through the main pulmonary artery MPA, which branches into the right pulmonary artery RPA and a left pulmonary artery LPA. The blood from the right pulmonary artery RPA further flows into various pulmonary artery branches PBR of the right pulmonary artery RPA.

The sensing device 20 generally comprises a proximal fixation element 22, a distal fixation element 24, a connecting element 26 mechanically coupling the proximal fixation element 22 to the distal fixation element 24, and a sensing element 28 mechanically coupled to the proximal fixation element 22 via another connecting element 30 opposite the connecting element 26 (i.e., the proximal fixation element 22 is between the connecting elements 26, 30). As shown in FIG. 2, the proximal fixation element 22 is firmly engaged with the wall of the right pulmonary artery RPA at a longitudinal location proximal to a side branch SBR, while the distal fixation element 24 is firmly engaged with the wall of the side branch SBR.

It can be appreciated that the use of two fixation elements 22, 24 effectively increases the anchoring force between the sensing device 20 and the vessel wall of the pulmonary arterial network in the longitudinal direction, thereby minimizing the chance that the sensing device 20 will migrate within the right pulmonary artery RPA after implantation. In addition, because the distal fixation element 24 is disposed in the side branch SBR transverse to the lumen of the right pulmonary artery RPA, the anchoring force between the sensing device 20 and the vessel wall of the pulmonary arterial network is also increased in a rotational direction about the longitudinal axis of the right pulmonary artery RPA.

Advantageously, the connecting element 26 allows the fixation elements 22, 24 to articulate relative to each other, so that the distal fixation element 24 can be more easily disposed within the pulmonary branch BR, while the proximal fixation element 22 is disposed within the right pulmonary artery RPA. Also, the only portion of the sensing device 20 that is within the bifurcation between the right pulmonary artery RPA and the side branch SBR is the relatively low profile connecting element 26. As a result, very little force will be applied to the sensing device 20 by the blood flowing into the side branch SBR from the right pulmonary artery RPA, thereby increasing the stability of the sensing device 20 within the right pulmonary artery RPA, as well as decreasing the chance of embolism that may otherwise result from clots formed by the obstructed blood flow. In addition, because the connecting element 26 has a low profile, future access to the side branch SBR is not significantly hindered, thereby preserving the capability of catheterizing the side branch SBR if necessary or desired.

The other connecting element 30 may be rigid, so as to maintain the sensing element 28 at a constant position, or can be flexible, so as to enable movement of the sensing element 28 within the vessel lumen. In the illustrated embodiment, the other connecting element 30 maintains the sensing element 28 between the vessel wall and the center of the vessel lumen, e.g., between 0.05 mm and 0.8r, where r is the radius of the vessel lumen. For example, for a lumen having a radius of r=10 mm, the sensing element 28 can be positioned at a distance between 0.05 mm and 8 mm from the vessel wall. In alternative embodiments, the sensing element 28 can be located either in contact with the vessel wall, at the vicinity of the vessel wall, or in any other convenient location within the vessel lumen. In these cases, the sensing element 28 may be connected directly to the proximal fixation element 22.

As illustrated in FIG. 2, each of the fixation elements 22, 24 has an expandable stent-like configuration having one or more struts coupled together to provide an outwardly urging radial force against the vessel wall. In the illustrated embodiment, the resilient struts are in an open radial zigzag configuration. Alternatively, the resilient struts may be in a closed radial zigzag configuration, as illustrated in FIG. 3. In either case, the expanded sizes, and in particular the diameters, of the fixation elements 22, 24 are individually selected to provide the necessary anchoring force within the respective vessel segments in which they are intended to be disposed; in this case, within the right pulmonary artery RPA and the side branch SBR, so that the expanded diameter of the proximal fixation element 22 will be greater than the expanded diameter of the distal fixation element 24.

In the illustrated embodiment, the struts of the fixation elements 22, 24 are composed of a suitable material that allows the fixation elements 22, 24 to self-expand radially outward in the absence of a compressive force. To this end, the fixation elements 22, 24 may be manufactured from a wire, a laser cut tube, or a chemical etched tube or metal sheet composed of a suitable biocompatible material, such as nickel-titanium alloy, stainless steel, titanium, or cobalt-based alloy, or to enhance the radio-opacity of the sensing device, tantalum, gold, platinum, or platinum-iridium. The fixation elements 22, 24 may alternatively be composed of a polymer, including a shape memory polymer with or without the addition of radio-opaque material (e.g., barium sulfate). The cross-section of the struts may be, e.g., round, oval, rectangular, or any convenient shape. The thickness of the struts may be in the range of 0.05-0.5 mm. The struts may optionally include ridges, barbs, or hooks for preventing migration of the sensing device 20 within the vessel lumen.

Each of the connecting elements 26, 30 may be composed of a suitable biocompatible material, such as nickel-titanium alloy, stainless steel, titanium, or cobalt-based alloy, or to enhance the radio-opacity of the sensing device, tantalum, gold, platinum, or platinum-iridium. The connecting elements 26, 30 may alternatively be composed of a polymer, including a shape memory polymer with or without the addition of radio-opaque material (e.g., barium sulfate).

In the illustrated embodiment, the sensing element 28 is a pressure sensor for monitoring blood pressure within the blood vessel. However, any known sensor can be used, including, but not limited to, an accelerometer, a wall motion sensor, a flow sensor, temperature sensor, oxygen sensor, glucose sensor, coagulation sensor, an electrical activity sensor, and pH sensor. In alternative embodiments, another operative element can be located either in contact with the vessel wall, at the vicinity of the vessel wall, or in any other convenient location within the vessel lumen. The operative element may be another sensing element different from the sensing element 28, or an energy source, such as a battery. For example, using an isolated electrical wire, the sensing element 28 can be electrically connected to a battery for enabling energy transfer from the battery to the sensing element 28. Further details describing the structure and function of implantable sensing elements are disclosed in U.S. Pat. Nos. 6,764,446 and 7,024,248, which are expressly incorporated herein by reference.

Referring now to FIG. 4, the sensing device 20 is shown implanted within the vessel network in a different configuration. In particular, the proximal fixation element 22 is firmly engaged with the wall of the right pulmonary artery RPA at a longitudinal location proximal to the side branch SBR, while the distal fixation element 24 is firmly engaged with the wall of the right pulmonary artery RPA at a longitudinal location distal to the side branch SBR.

As previously described with respect to FIG. 2, the use of two fixation elements 22, 24 effectively increases the anchoring force between the sensing device 20 and the vessel wall of the pulmonary arterial network in the longitudinal direction, thereby minimizing the chance that the sensing device 20 will migrate within the right pulmonary artery RPA after implantation. In addition, because the fixation elements 22, 24 articulate relative to each other, the non-uniformity of the diameter along the right pulmonary artery RPA does not significantly diminish the anchoring capability of the sensing device 20. While the configuration shown in FIG. 4 does not use the side branch SBR as an anchoring mechanism, it does accommodate the side branch SBR by only locating the low-profile connecting element 26 at the bifurcation. The connecting element 26 may either cross the side branch SBR, or may even be offset from the side branch SBR to maintain the side branch SBR totally patent without crossing it.

Referring to FIG. 5, another implantable sensing device 40 constructed in accordance with the present inventions will now be described. The sensing device 40 is similar to the previously sensing device 40, with the exception that the sensing element 28 is coupled between the fixation elements 22, 24. As can be seen, the sensing element 28 is suspended in the lumen of the right pulmonary artery RPA at the bifurcation. Preferably, the sensing element 28 is located as remotely as possible from the bifurcation to minimize blockage of the side branch SBR, which may otherwise increase the chances of migration and/or embolism. An optional connecting element 34 may be mechanically coupled between the fixation elements 22, 24 to provide additional support, and thus, anchoring force to the sensing device 40.

Referring to FIG. 6, another implantable sensing device 50 constructed in accordance with the present inventions will now be described. The sensing device 50 is similar to the previously described sensing device 20, with the exception that the sensing element 28 is mounted to the connecting element 26 between the fixation elements 22, 24. As shown, the fixation element 22 is firmly engaged with the wall of the right pulmonary artery RPA at a longitudinal location distal to a side branch SBR, while the fixation element 24 is firmly engaged with the wall of the side branch SBR. As can be seen, the sensing element 28 is suspended in the lumen of the right pulmonary artery RPA at the bifurcation. Preferably, the sensing element 28 is located as remotely as possible from the bifurcation to minimize blockage of the side branch SBR, which may otherwise increase the chances of migration and/or embolism.

While the implantable sensing devices 20, 40, and 50 have been described as having only two fixation elements and only one sensing element, an implantable sensing device constructed in accordance with the present inventions can have more than two fixation elements and more than one sensing element. For example, referring to FIG. 7, an implantable sensing device 60 generally comprises a proximal fixation element 62, a medial fixation element 64, a distal fixation element 66, a first connecting element 68 mechanically coupling the proximal fixation element 62 to the medical fixation element 64, a second connecting element 70 mechanically coupling the distal fixation element 66 to the medical fixation element 64, and three sensing elements 72, 74, 76 mechanically coupled to the respective fixation elements 62, 64, 66 via three connecting elements 78, 80, 82. The fixation elements 62, 64, 66, connecting elements 78, 80, 82, and sensing elements 72, 74, 76 can be similarly constructed and function in the same manner as the same-named components described above.

Figure 7:
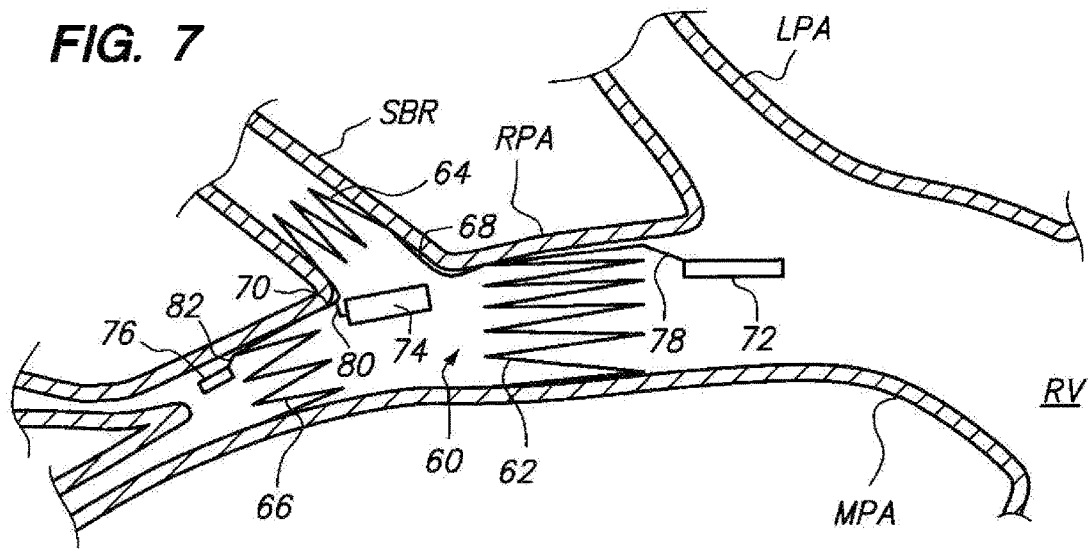
FIG. 7 is a side view of a sixth sensing device arrangement within the pulmonary arterial network in accordance with the present inventions.

As shown in FIG. 7, the proximal fixation element 62 is firmly engaged with the wall of the right pulmonary artery RPA at a longitudinal location proximal to the side branch SBR, the medial fixation element 64 is firmly engaged with the wall of the side branch SBR, and the distal fixation element 66 is firmly engaged with the wall of the right pulmonary artery RPA at a longitudinal location distal to the side branch SBR. Thus, it can be appreciated that the use of three fixation elements, one of which is disposed in the side branch SBR, further increases the anchoring force between the sensing device 60 and the vessel wall of the pulmonary arterial network in the longitudinal and rotational directions, thereby further minimizing the chance that the sensing device 20 will migrate within the right pulmonary artery RPA after implantation. In addition, the use of three sensing elements increases the volume and/or types of information sensed within the right pulmonary artery RPA.

Figure 8:
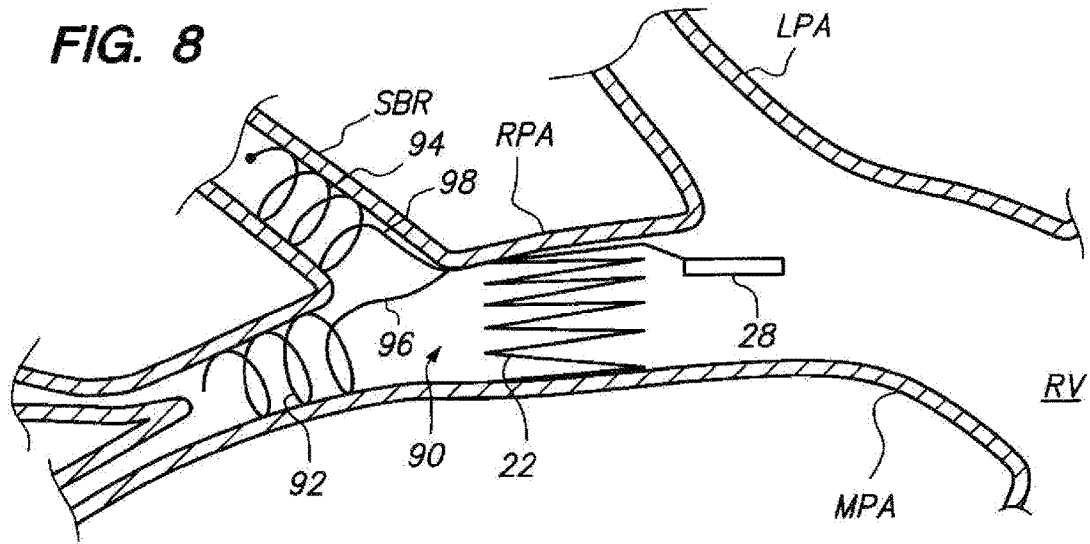
FIG. 8 is a side view of a seventh sensing device arrangement within the pulmonary arterial network in accordance with the present inventions.

While the fixation elements have thus far been described as having stent-like configurations, the fixation elements can have other configurations (which may be different between fixation elements of the same device) suitable for firmly engaging the walls of an anatomical vessel. For example, referring to FIG. 8, an implantable sensing device 90 is similar to the sensing device 20 illustrated in FIG. 2, with the exception that, instead of having a distal fixation element 24 in a stent-like configuration, it comprises two distal fixation elements 92, 94 in coil-like configurations, which are mechanically coupled to the proximal fixation element 22 via respective connecting elements 96, 98. Each of the coiled fixation elements 92, 94 comprises a single wire, which can have the same cross-section and be composed of the same material as the struts of the fixation elements 22, 24 described above with respect to FIG. 2. As shown, the fixation element 92 is firmly engaged with the wall of the right pulmonary artery RPA at a location distal to the side branch SBR, and the fixation element 94 is firmly engaged with the wall of the side branch SBR, thereby providing the same anchoring advantages as the implantable sensing device 20 of FIG. 6.

Figure 9:
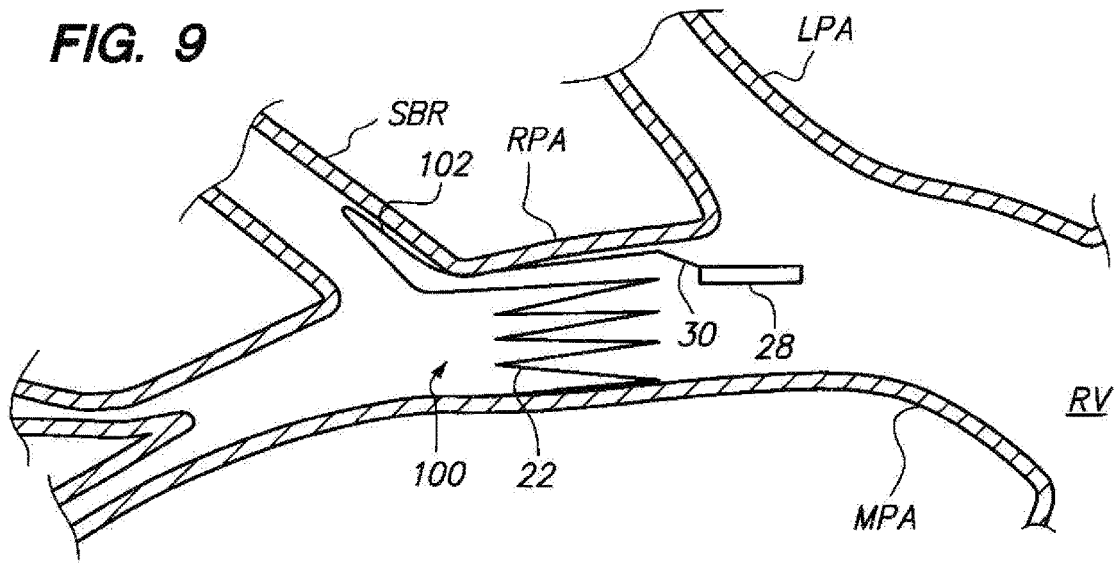
FIG. 9 is a side view of an eighth sensing device arrangement within the pulmonary arterial network in accordance with the present inventions.

Implantable sensing devices constructed in accordance with the present invention can have stabilization elements other than fixation elements. For example, referring to FIG. 9, an implantable sensing device 100 is similar to the sensing device 20 illustrated in FIG. 2, with the exception that, instead of a distal fixation element 24, a stabilization element in the form of a flange 102 is mechanically coupled to the proximal fixation element 22. In the illustrated embodiment, the flange 102 is formed by looping a strut of the fixation element 22 back onto itself. The flange 102 is pre-shaped (e.g., by an appropriate thermal treatment of a nickel-titanium alloy), such that it extends at an angle from the fixation element 22 (i.e., transversely or obliquely to the longitudinal axis of the fixation element 22) into contact with the wall of the side branch SBR, thereby increasing the anchoring force between the sensing device 20 and the pulmonary arterial network in both the longitudinal and rotational directions. Preferably, the flange 102 is composed of a material rigid enough to provide the necessary stability to the sensing device 100.

Figure 10:
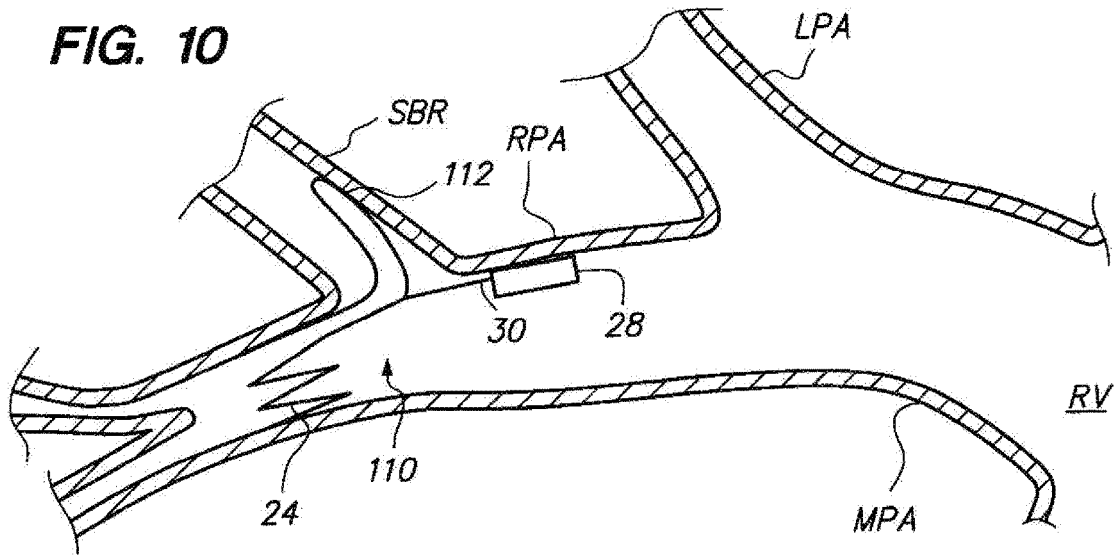
FIG. 10 is a side view of a ninth sensing device arrangement within the pulmonary arterial network in accordance with the present inventions.

Referring now to FIG. 10, another implantable sensing device 110 will be described. The sensing device 110 is similar to the previously described sensing device 100 of FIG. 9, with the exception that, instead of a proximal fixation element 22, it includes the distal fixation element 24 configured to firmly engage the wall of the right pulmonary artery RPA at a location distal to the side branch SBR. As with the sensing device 100, the sensing device 110 comprises a flange 112 mechanically coupled to the distal fixation element 24 and shaped, such that it extends at an angle from the fixation element 24 into contact with the wall of the side branch SBR, thereby increasing the anchoring force between the sensing device 100 and the pulmonary arterial network in both the longitudinal and rotational directions. The flange 112 may be formed by looping a strut of the fixation element 24 back onto itself, and is preferably composed of a material rigid enough to provide the necessary stability to the sensing device 110.

Figure 11:
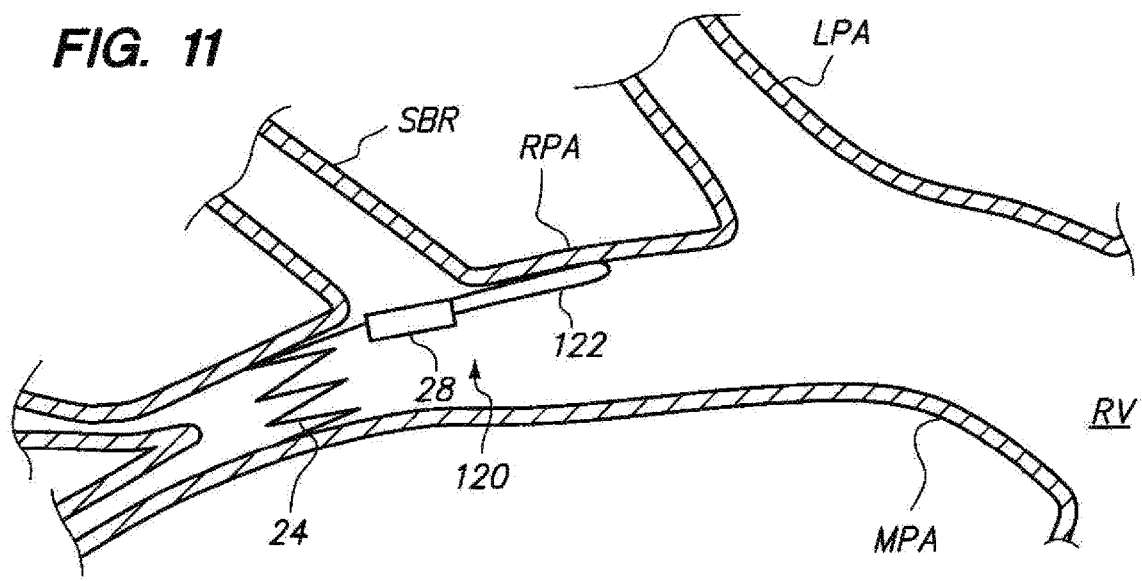
FIG. 11 is a side view of a tenth sensing device arrangement within the pulmonary arterial network in accordance with the present inventions.

Referring now to FIG. 11, still another implantable sensing device 120 will be described. The sensing device 120 is similar to the previously described sensing device 110 of FIG. 10, with the exception that it includes a flange 122 that is not pre-shaped to extend within the side branch SBR. Rather, the flange 122 is relatively straight, so that it remains within the lumen of the right pulmonary artery RPA. In addition, the sensing element 28 is mechanically coupled between the distal fixation element 24 and the flange 122. Although the flange 122 is not designed to extend within the side branch SBR, and thus, does not significantly increase the anchoring force in a rotational direction about the longitudinal axis of the right pulmonary artery RPA, the flange 122 abuts the wall of the right pulmonary artery RPA, thereby preventing the sensing element 28 from hinging into the side branch SBR in response to the flow of blood from the right pulmonary artery RPA into the side branch SBR.

Figure 12:
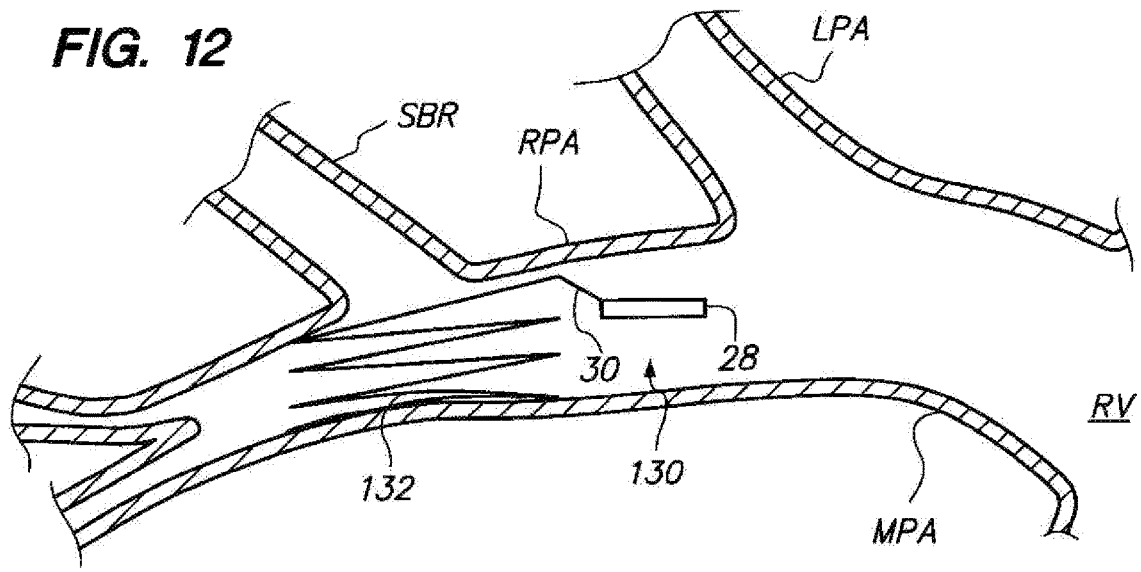
FIG. 12 is a side view of an eleventh sensing device arrangement within the pulmonary arterial network in accordance with the present inventions.
Figure 13:
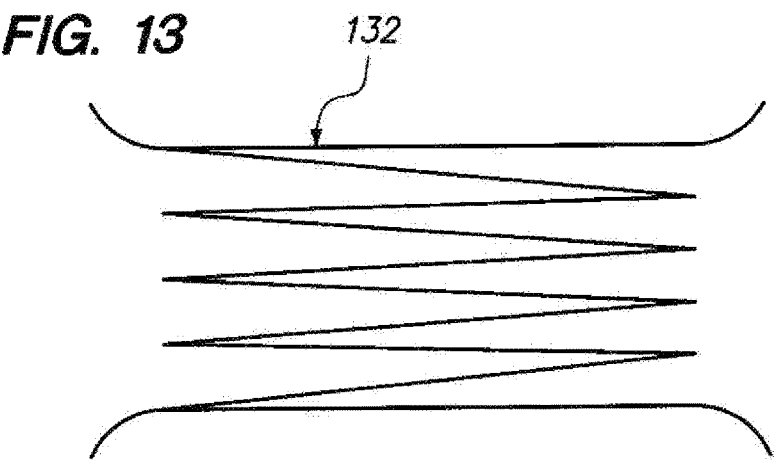
FIG. 13 is a side view of an alternative embodiment of a fixation element used in the eleventh sensing device arrangement of FIG. 12.
Figure 14:
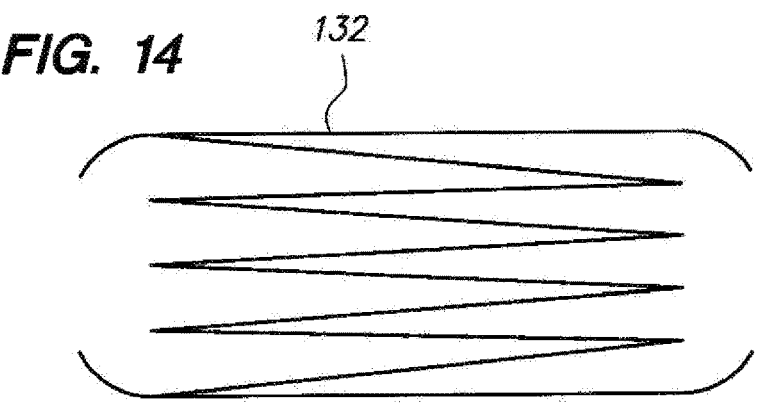
FIG. 14 is a side view of another alternative embodiment of fixation element used in the eleventh sensing device arrangement of FIG. 12.

Referring to FIG. 12, yet another implantable sensing device 130 constructed in accordance with the present inventions will now be described. The sensing device 130 comprises a single fixation element 132 and the previously described sensing element 28 mechanically coupled to the fixation element 132. The fixation element 132 is similar to either of the previously described fixation elements 22, 24 in FIG. 2, with the exception that the length of the fixation element 132 is increased to allow it to cross the side branch SBR. For example, the length of the fixation element 132 may be equal to or greater than 35 mm. The increased length of the fixation element 132 increases the anchoring force between the sensing device 130 and the vessel wall of the pulmonary arterial network. To further increase the anchoring capability of the fixation element 132, the proximal and distal edges of the fixation element 132 may be curved radially outward, as illustrated in FIG. 13, to provide a gripping force against the vessel wall that decreases longitudinal migration of the sensing device 130. Alternatively, the proximal and distal edges of the fixation element 132 may be curved radially inward, as illustrated in FIG. 14. In this manner, the resilient spring force of the fixation element 132 can be increased, thereby increasing its anchoring capability, without concern that the edges of the fixation element 132 will damage or otherwise irritate the wall of the right pulmonary artery RPA.

Figure 15:
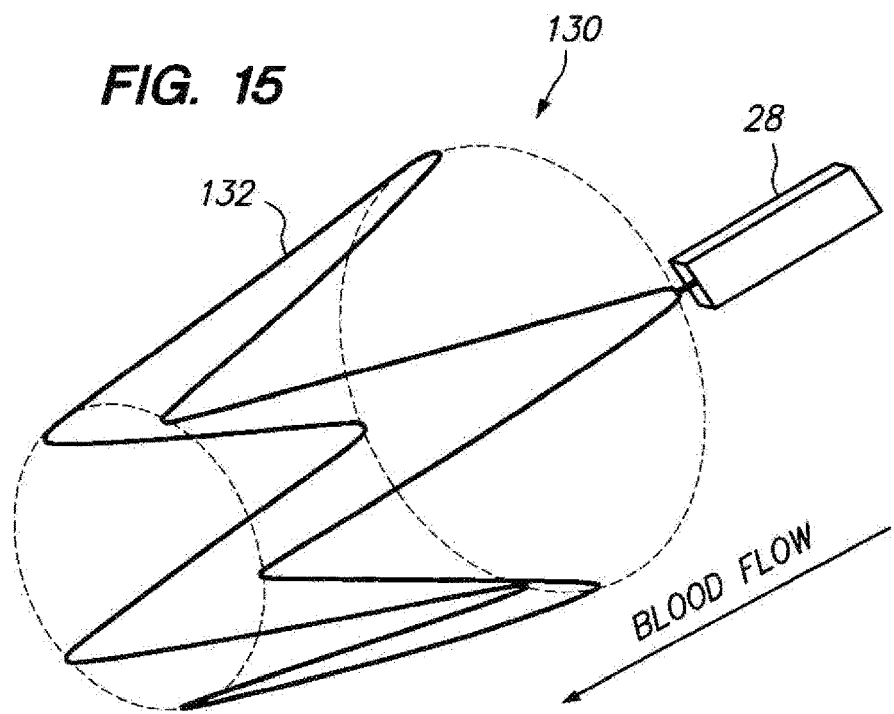
FIG. 15 is a side view of a still another alternative embodiment of a fixation element used in the eleventh sensing device arrangement of FIG. 12.
Figure 16:
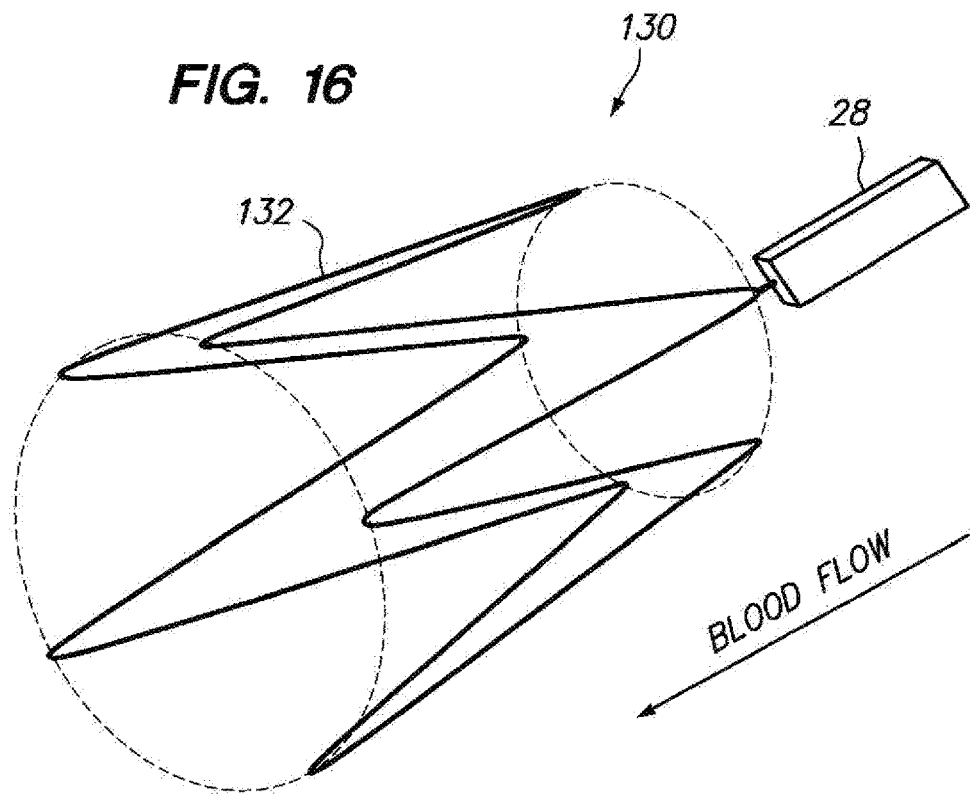
FIG. 16 is a side view of yet another alternative embodiment of fixation element used in the eleventh sensing device arrangement of FIG. 12.
Figure 17:
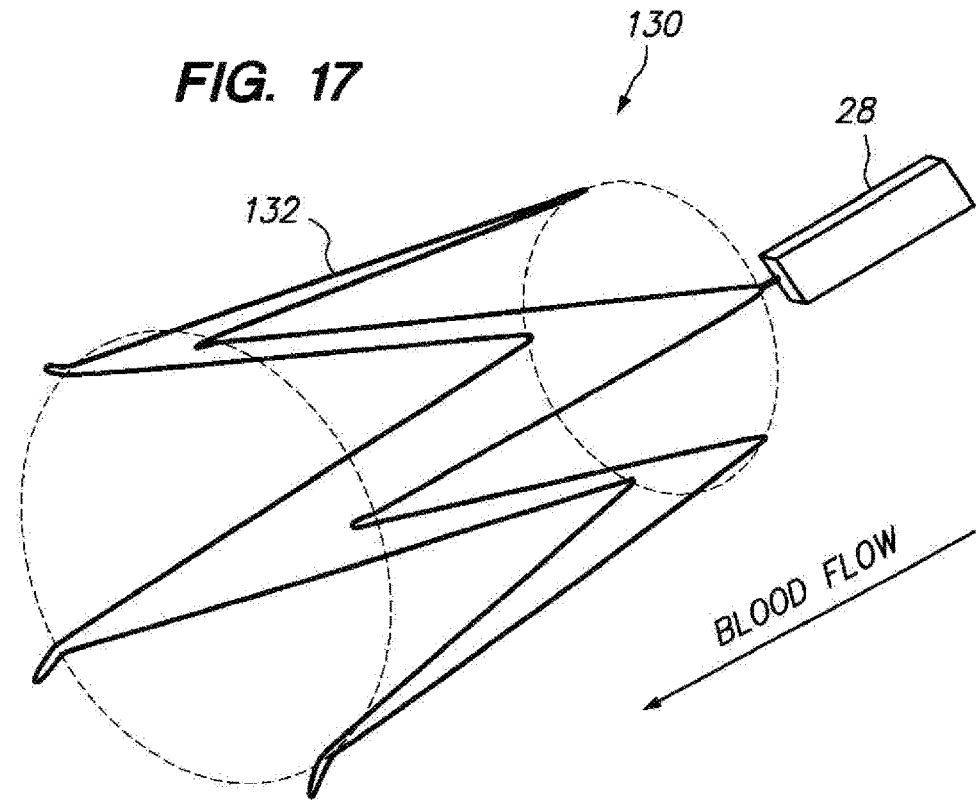
FIG. 17 is a side view of yet another alternative embodiment of fixation element used in the eleventh sensing device arrangement of FIG. 12.

Notably, if the fixation element 132 is relatively uniform diameter along its length, its implantation into a conically shaped vessel may induce a spring forces that tends to push the sensing device 130 in the proximal direction. To address this, the fixation element 132 may be pre-shaped to have a conical geometry similar to the conical shape of the vessel (e.g., conical angle of 0-400 and length of 10-35 mm), as illustrated in FIG. 15. In this case, the fixation element 132 will be arranged in the vessel, such that the larger diameter of the fixation element 132 coincides with the large diameter of the vessel, and the small diameter of the fixation element 132 coincides with the small diameter of the vessel. Thus, the non-loaded fixation element 132 will have less of a tendency to move from its intended position. Alternatively, the fixation element 132 may be arranged as a mirror image of the vessel, as illustrated in FIG. 16. That is, the large diameter of the fixation element 132 coincides with the small diameter of the vessel, and the small diameter of the fixation element 132 coincides with the large diameter of the vessel. In this case, the shape and configuration of the fixation element 132 will straighten out the vessel, so that it is no longer conically shaped. Alternatively, as illustrated in FIG. 17, the distal edges of the fixation element 132 may be curved radially outward to provide a gripping force against the vessel wall that decreases longitudinal migration of the sensing device 130. Notably, these conical fixation element concepts can be applied to any of the previous embodiments.

The afore-described sensing devices can be delivered and implanted within the pulmonary arterial network of the patient using any suitable means, such as, e.g., a deliver catheter. For example, referring to FIGS. 18A-18D, a method of delivering the sensing device 20 within the pulmonary arterial network of a patient will now be described. The delivery system 150 includes a flexible catheter 152 configured for being delivered through the vasculature of a patient, and a pusher element 154 slidably disposed within the lumen of the catheter 152. The sensing device 20, and in particular, the sensing element 28, is detachably coupled to the distal end of the pusher element 154 using suitable means, such as a mechanical interference or electrolytic arrangement.

In the illustrated embodiment, the pusher element 154 is capable of being rotated relative to the catheter 152, so that the sensing device 20 can be implanted within the pulmonary arterial network in a specific circumferential location. That is, it may be desirable for the sensing element 28 to be located at the top of the vessel wall or at the bottom of the vessel wall. It may also be desirable to maintain the rotational orientation of the fixation elements 22, 24 relative to each other, so that the connecting element 26 runs along one side of the vessel wall—instead of traversing the lumen of the vessel in the case where the one of the fixation elements 22, 24 is rotationally misaligned by 180 degrees.

To this end, a radio-opaque marker 156 is disposed on the sensing device 20 in a manner that allows the orientation of the sensing device 20 to be determined via fluoroscopic imaging. The radio-opaque marker 156 may take the form of a material (e.g., platinum, gold, tantalum, or other commonly used radio-opaque material) coated on the sensing element 28 (as shown in the figures), or may take the form of a wire composed of the same material, which may, e.g., be crimped onto one or both of the fixation element 22, 24, or may even take the form of the connecting element 26 itself.

In the illustrated method, the sensing device 20 will be delivered into the pulmonary arterial network in the configuration illustrated in FIG. 2; i.e., with the distal fixation element 24 disposed within the side branch SBR and the proximal fixation element 24 disposed in the right pulmonary artery RPA at a longitudinal location proximal to the side branch SBR. As shown in FIG. 18A, the catheter 152 is advanced from the right ventricle RV of the heart, through the main pulmonary artery MPA, and into the lumen of the right pulmonary artery RPA. As can be seen, the sensing device 20 is loaded into the delivery catheter 152, such that the distal fixation element 24 will be deployed prior to the proximal fixation element.

As shown in FIG. 18B, the distal end of the catheter 152 is advanced into the side branch SBR (or alternatively, at the bifurcation within the right pulmonary artery RPA, but deflected towards the opening of the side branch SBR), and the pusher element 154 is distally advanced to push the distal fixation element 24 out from the catheter 152 and into the lumen of the side branch SBR. As previously discussed, the distal fixation element 24 is composed of a resilient material that causes it to self-expand in the absence of a compressive force. As a result, the distal fixation element 24 will automatically expand radially outward into firm contact with the wall of the side branch SBR once it is deployed from the catheter 152. Alternatively, if the distal fixation element 24 is not capable of self-expanding, a balloon can be used to radially expand the distal fixation element 24 into firm contact with the vessel wall.

Figure 18C:
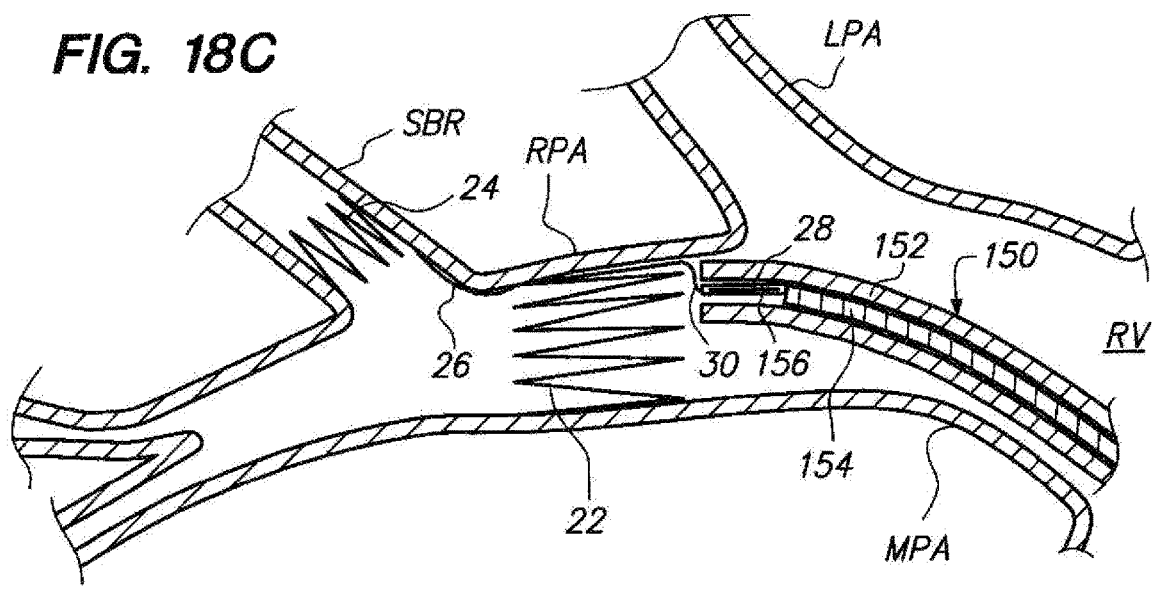
Figure 18D:
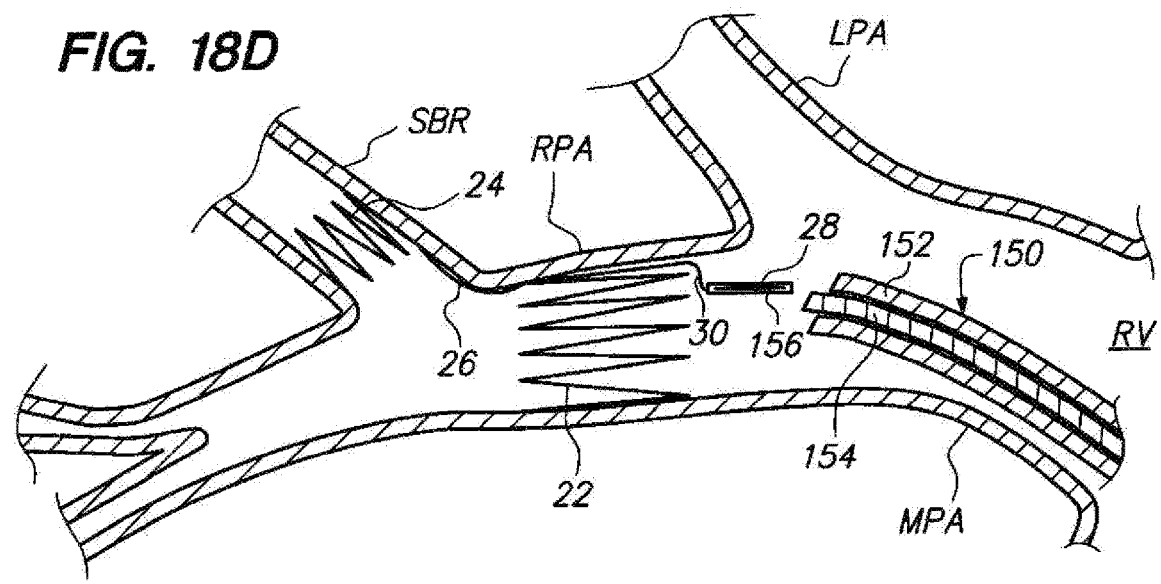

As shown in FIG. 18C, the catheter 152 is then pulled in the proximal direction, so that the distal end of the catheter 152 is located within the right pulmonary artery RPA, and the pusher element 154 is distally advanced to push the proximal fixation element 24 out from the catheter 152 into the lumen of the right pulmonary artery RPA, where it automatically expands radially outward (or alternatively radially expands with the aid of a balloon) into firm contact with the wall of the right pulmonary artery RPA. As shown in FIG. 18D, the pusher element 154 is distally advanced further to push the sensing element 28 out from the catheter 152 into the lumen of the right pulmonary artery RPA, and the pusher element 154 is detached from the sensor element 28.

Similar delivery techniques can be used to form the configurations within the pulmonary arterial network illustrated in FIGS. 3-8. With respect to the configurations illustrated in FIGS. 9 and 10, the sensing devices can be implanted in the pulmonary arterial network by dragging the flange of the sensing device proximally or distally within the right pulmonary artery RPA until the flange locates itself into the side branch SBR, as illustrated in FIGS. 19A-19H.

Figure 19A:
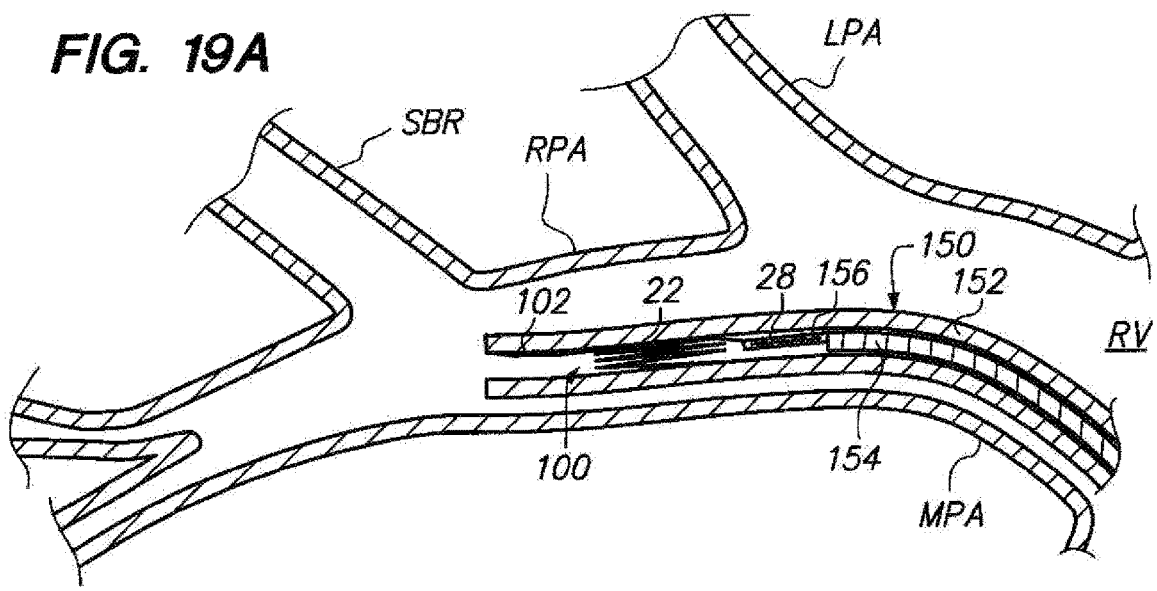
Figure 19B:
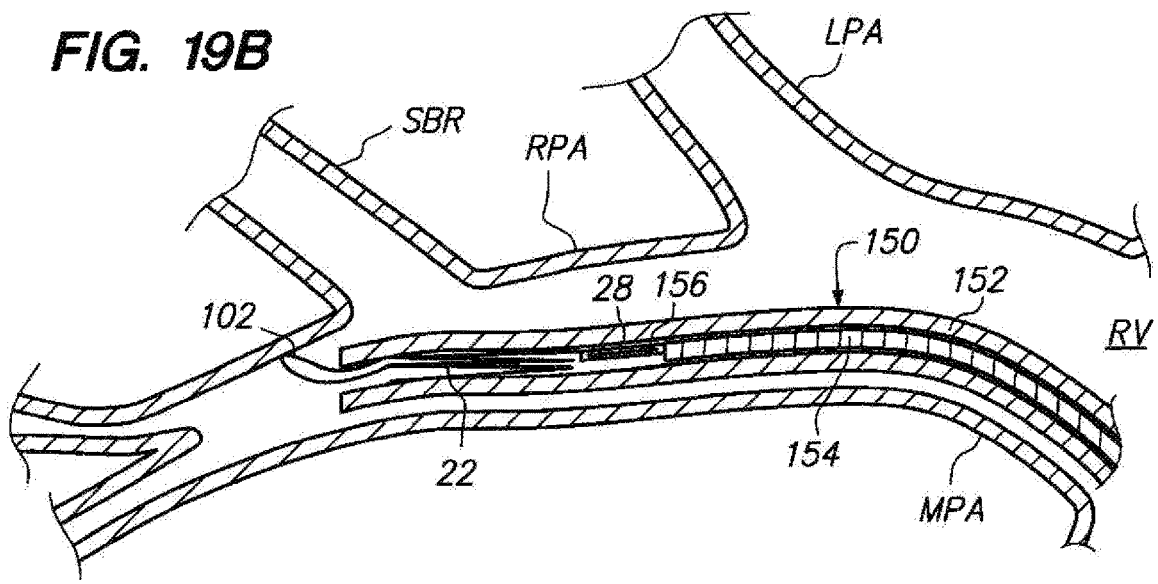

For example, as shown in FIG. 19A, the sensing device 100 is loaded into the delivery catheter 152, such that the flange 102 will be deployed prior to the fixation element 22. As shown in FIG. 19B, the distal end of the catheter 152 is advanced to a location in the right pulmonary artery RPA distal to the side branch SBR, and the pusher element 154 is distally advanced to push the flange 102 out from the catheter 152 and into contact with the wall of the right pulmonary artery RPA. As shown in FIG. 19C, the catheter 152 is pulled in the proximal direction until the flange 102 catches within the side branch SBR.

As an alternative to the steps illustrated in FIGS. 19B and 19C, the distal end of the catheter 152 can be advanced to a location in the right pulmonary artery RPA proximal to the side branch SBR, and the pusher element 154 is distally advanced to push the flange 102 out from the catheter 152 and into contact with the wall of the right pulmonary artery RPA, as illustrated in FIG. 19D, after which the catheter 152 is pushed in the distal direction until the flange 102 catches within the side branch SBR.

Figure 19E:
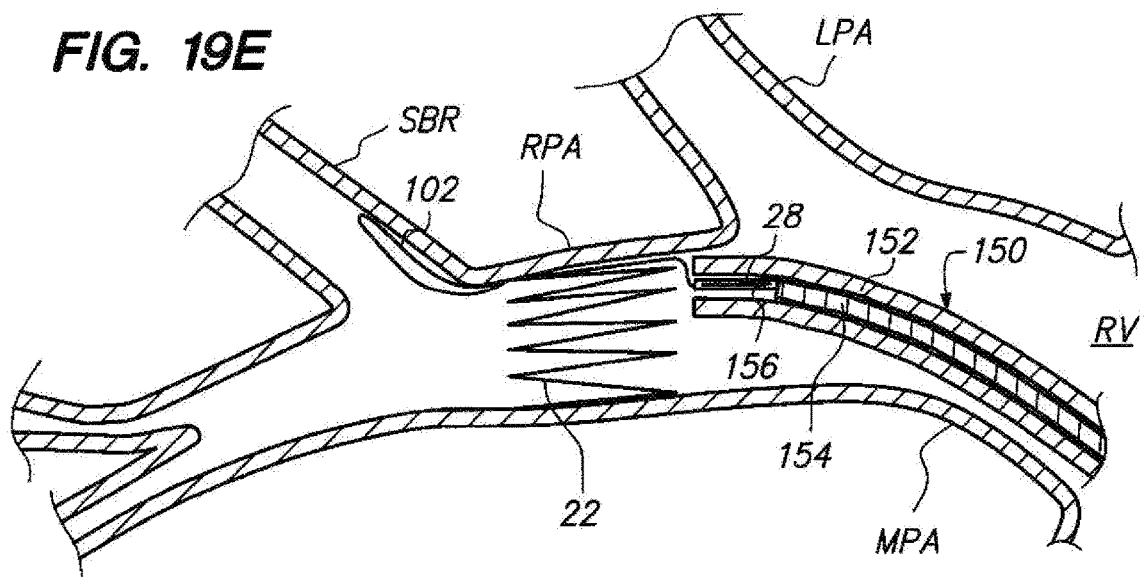
Figure 19F:
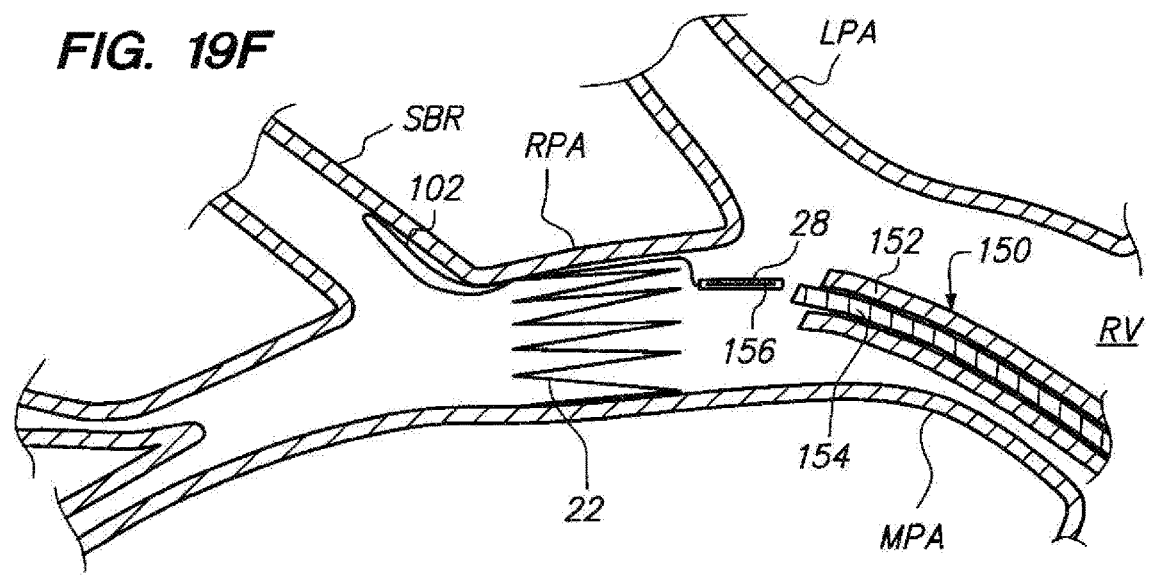

In any event, once the flange 102 is located within the side branch SBR, the pusher element 154 is distally advanced to push the fixation element 22 out from the catheter 152 into the lumen of the right pulmonary artery RPA, where it automatically expands radially outward into firm contact with the wall of the right pulmonary artery RPA, as shown in FIG. 19E. The pusher element 154 is distally advanced further to push the sensing element 28 out from the catheter 152 into the lumen of the right pulmonary artery RPA, and the pusher element 154 is detached from the sensor element 28, as illustrated in FIG. 19F.

A similar method can be utilized to implant the sensing device 110 of FIG. 10, with the exception that the fixation element 24 will need to be deployed out from the catheter 152 before the flange 112, as illustrated in FIG. 19G. In this case, before the sensing element 28 is detached from the pusher element 154, the catheter 152 is pulled in the proximal direction, thereby displacing the entire sensing device 110, including the expanded fixation element 24, within the right pulmonary artery RPA until the flange 112 is located within the side branch SBR, as illustrated in FIG. 19H. After the sensing device 110 is properly located, the pusher element 154 is detached from the sensor element 28.

The sensing device 120 illustrated in FIG. 11 can be implanted within the pulmonary arterial network simply by deploying the fixation element 24 in the right pulmonary artery RPA at a location distal to the side branch SBR, pulling the catheter 152 in the proximal direction to deploy the sensor 28 and flange 122 within the right pulmonary artery RPA, and detaching the pusher element 154 from the sensor element 28. The sensing device 130 illustrated in FIG. 12 can be implanted within the pulmonary arterial network simply by deploying the fixation element 24 in the right pulmonary artery RPA at a location at the side branch SBR, pulling the catheter 152 in the proximal direction to deploy the sensor 28 within the right pulmonary artery RPA, and detaching the pusher element 154 from the sensor element 28.

As previously discussed, the distal fixation element 24 is composed of a resilient material that causes it to self-expand in the absence of a compressive force. As a result, the distal fixation element 24 will automatically expand radially outward into firm contact with the wall of the side branch SBR once it is deployed from the catheter 152. Alternatively, if the distal fixation element 24 is not capable of self-expanding, a balloon can be used to radially expand the distal fixation element 24 into firm contact with the vessel wall.

While the sensing devices have been illustrated and described as being implanted within the pulmonary artery PA, it should be appreciated that the sensing devices can be implanted in other blood vessels of the patient's body, e.g., the vena cava, pulmonary vein, coronary sinus, aorta, subclavian artery, iliac artery, and carotid artery. While the inventive method lends itself well to the implantation of the sensing devices in blood vessels, it should be appreciated that the sensing devices can be implanted in other anatomical vessels, such as the esophagus, intestine, trachea, bronchial tubes, etc. Lastly, while the present implantation techniques have been described with respect to sensing devices, the same implantation techniques can be utilized to implant therapeutic devices (e.g., a drug releasing device or neurostimulator for treating arrhythmia, pain, or neurological disturbances or for stimulating the gastrointestinal system or urinary system) within the anatomical vessels of patients.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed:

1. A method of implanting a sensing device within an anatomical vessel network having a main anatomical vessel and an anatomical vessel branch of the main anatomical vessel, the method comprising:
    expanding a fixation element coupled to a sensing element of the device, at a first end of the sensing element, into firm contact with the wall of the main anatomical vessel at a longitudinal location proximal to and spaced apart from an ostium of the anatomical vessel branch; and
    expanding a stabilization element coupled to the sensing element, at a second end of the sensing element, into firm contact with the wall of the main anatomical vessel at a longitudinal location distal to and spaced apart from the ostium of the anatomical vessel branch, wherein the stabilization element is a flange that consists of a single wire loop coupled, at a first end of the single wire loop, to the second end of the sensing element, extending away from the second end of the sensing element, curving back toward the second end of the sensing element, and coupled, at a second end of the single wire loop, to the second end of the sensing element; and wherein only the sensing element is positioned at the ostium of the anatomical vessel branch.

2. The method of claim 1, wherein the anatomical vessel network is a blood vessel network.

3. The method of claim 2, wherein the main anatomical vessel is a right pulmonary artery.

4. The method of claim 1, wherein the fixation element is selected from the group consisting of a stent and a coil.

5. The method of claim 1, wherein the sensing element of the device is located within the main anatomical vessel when the fixation and stabilization elements are firmly engaged with the wall of the main anatomical vessel.

6. The method of claim 1, further comprising measuring one or more of a pressure, acceleration, wall motion, fluid flow, temperature, oxygen level, glucose level, coagulation, electrical activity, and pH level within the anatomical vessel.

7. The method of claim 1, further comprising wirelessly transmitting sensed information from the sensing device.

8. An implant for sensing parameters within an anatomical vessel network of a patient, comprising:
    a fixation element having an expanded geometry for firmly engaging a wall of the vessel network at a first longitudinal location;
    a stabilization element having an expanded geometry for firmly engaging the wall of vessel network at a second longitudinal location, wherein the stabilization element is a flange, the flange consisting of a single wire loop; and
    a pressure sensing element mechanically coupled, on a first side of the pressure sensing element and via a rigid connecting element, to the fixation element, and mechanically coupled, on a second side of the pressure sensing element, to the stabilization element, wherein the rigid connecting element is configured to suspend the pressure sensing element inwardly a distance apart from the vessel wall such that blood flows unobstructed along a portion of the vessel network located between the wall and the sensing element; and
    wherein the flange is coupled, at a first end of the single wire loop, to the second side of the pressure sensing element, extending away from the second side of the pressure sensing element, curving back toward the second side of the pressure sensing element, and coupled, at a second end of the single wire loop, to the second side of the pressure sensing element.

9. The implant of claim 8, wherein the vessel network is a blood vessel network.

10. The implant of claim 9, wherein at least one of the first and second longitudinal locations is in a right pulmonary artery.

11. The implant of claim 8, wherein the vessel network has differing diameters at the first and second longitudinal locations.

12. The implant of claim 8, wherein the first and second longitudinal locations are in a single anatomical vessel.

13. The implant of claim 8, wherein the first longitudinal location is in a main anatomical vessel, and the second longitudinal location is in an anatomical vessel branch of the main anatomical vessel.

14. The implant of claim 8, wherein the fixation element is selected from the group consisting of a stent and a coil.

15. The implant of claim 8, further comprising a transmitter configured for wirelessly transmitting information sensed by the sensing element to a remote receiver.

* * * * *